US011352370B2

(12) United States Patent
Sebti et al.

(10) Patent No.: US 11,352,370 B2
(45) Date of Patent: Jun. 7, 2022

(54) MUTANT KRAS INHIBITORS

(71) Applicants: H. LEE MOFFITT CANCER CENTER AND RESEARCH INSTITUTE, INC., Tampa, FL (US); TORREY PINES INSTITUTE FOR MOLECULAR STUDIES, Port st. Lucie, FL (US)

(72) Inventors: Said M. Sebti, Tampa, FL (US); Yangmei Li, Port St. Lucie, FL (US); Richard A. Houghten, Port St. Lucie, FL (US)

(73) Assignees: H. Lee Moffitt Cancer Center and Research Institute, Inc., Tampa, FL (US); Torrey Pines Institute for Molecular Studies, Port St. Lucie, FL (US)

( * ) Notice: Subject to any disclaimer, the term of this patent is extended or adjusted under 35 U.S.C. 154(b) by 0 days.

(21) Appl. No.: 16/927,517

(22) Filed: Jul. 13, 2020

(65) Prior Publication Data
US 2021/0115063 A1 Apr. 22, 2021

Related U.S. Application Data

(63) Continuation of application No. 16/540,757, filed on Aug. 14, 2019, now Pat. No. 10,711,014, which is a continuation of application No. 15/568,931, filed as application No. PCT/US2016/029180 on Apr. 25, 2016, now Pat. No. 10,421,764.

(60) Provisional application No. 62/152,333, filed on Apr. 24, 2015.

(51) Int. Cl.
*C07D 221/16* (2006.01)
*C07D 401/04* (2006.01)
*C07D 401/14* (2006.01)
*A61K 31/429* (2006.01)
*A61P 35/00* (2006.01)
*C07D 513/04* (2006.01)

(52) U.S. Cl.
CPC .......... *C07D 513/04* (2013.01); *A61K 31/429* (2013.01); *A61P 35/00* (2018.01); *C07C 2601/14* (2017.05); *C07C 2601/16* (2017.05); *C07C 2602/10* (2017.05)

(58) Field of Classification Search
CPC .. C07D 221/16; C07D 401/04; C07D 401/14; A61K 31/429; A61P 35/00
See application file for complete search history.

(56) References Cited

U.S. PATENT DOCUMENTS

| 2,969,369 | A | 1/1961 | Peter |
|---|---|---|---|
| 4,162,253 | A | 7/1979 | Acheson et al. |
| 7,501,430 | B2 | 3/2009 | Lapierre et al. |
| 2009/0021645 | A1 | 1/2009 | Hayashi et al. |
| 2015/0087628 | A1 | 3/2015 | Shokat et al. |

OTHER PUBLICATIONS

International Search Report and Written Opinion issued in International Application No. PCT/US2016/29180 dated Aug. 8, 2016.
Pubchem, "Compound Summary for CID684820", created Jul. 7, 2005, accessed Jun. 12, 2016.
Ferns, et al., "CAPLUS", Anales inst. farmacol. espan, 1958.
Wilson, et al., "CAPLUS", Journal of the Chemical Society, 1956.

*Primary Examiner* — Bruck Kifle
(74) *Attorney, Agent, or Firm* — Meunier Carlin & Curfman LLC

(57) ABSTRACT

Compositions and methods for inhibits the binding of GTP to oncogenic mutant KRas are disclosed. These compositions may be used in method to treat a subject with cancer. In particular, the compositions may be used to treat cancers involving overactive Ras signaling.

15 Claims, 21 Drawing Sheets

MUTANT KRAS INHIBITORS

CROSS REFERENCE TO RELATED APPLICATIONS

This application is a continuation of U.S. application Ser. No. 16/540,757, filed Aug. 14, 2019, which is a divisional of U.S. application Ser. No. 15/568,931, filed Oct. 24, 2017, which is a 371 U.S. National Phase of International Application PCT/US2016/029180, filed Apr. 25, 2016, which claims the benefit of priority to U.S. Provisional Application 62/152,333, filed Apr. 24, 2015, each of which are hereby incorporated by reference herein in their entireties.

BACKGROUND

Ras activation is catalyzed by GEFs such as SOS that exchange bound GDP for GTP, whereas Ras inactivation is catalyzed by GAPs leading to the hydrolysis of GTP to GDP. Oncogenic mutations in KRas impair GTP hydrolysis, leading to a constitutively activated, GTP-bound mt KRas, which contributes significantly to human cancer pathogenesis and patient tumor resistance. The purpose of this research program is to identify small molecules that bind mt KRas directly and shift its state from GTP to GDP, inhibiting its ability to bind its effectors. Although the picomolar affinity for GTP and the difficulty in identifying allosteric sites have made it hard to target directly Ras, evidence for the feasibility of targeting Ras has been reported. Recently, one report provided compelling evidence of small molecules that can bind covalently to Cys, occupy a pocket composed largely of the switch II region of G12C mt KRas, and inhibit the interaction of Ras-GTP with its effectors. Other recent reports identified small molecules that inhibited SOS-mediated nucleotide exchange by binding to a pocket adjacent to the switch I/II regions of KRas. Although compounds that exclusively inhibit GDP exchange for GTP may be effective in tumors that depend on wt Ras for their malignancy, they are less likely to affect tumors with mt GTP-bound Ras.

SUMMARY

Compositions and methods for inhibiting the binding of GTP to oncogenic mutant KRas are disclosed. These compositions may be used in method to treat a subject with cancer. In particular, the compositions may be used to treat cancers involving overactive Ras signaling.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
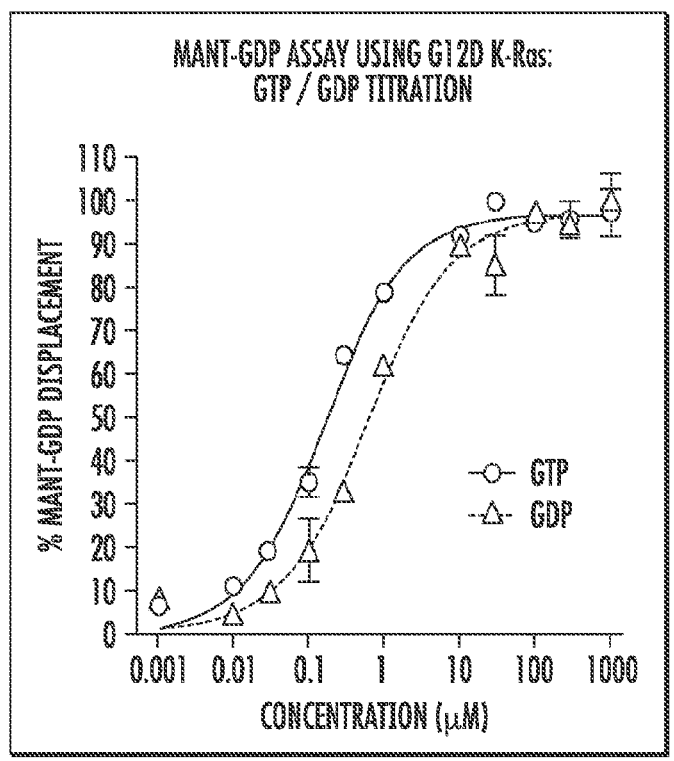
FIG. 1A and FIG. 1B show optimization of the mant-GDP (FIG. 1A) and the GST-RBG (FIG. 1B) assays

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a patient can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "cancer" or "malignant neoplasm" refers to a cell that displays uncontrolled growth, invasion upon adjacent tissues, and often metastasis to other locations of the body.

The cancer of the disclosed methods can be any cell in a subject undergoing unregulated growth, invasion, or metastasis that involves overactive Ras signaling. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ indicates in each case the possible number of carbon atoms in the group.

The term "alkyl," as used herein, refers to saturated straight, branched, primary, secondary or tertiary hydrocarbons, including those having 1 to 20 atoms. In some examples, alkyl groups will include $C_1$-$C_{12}$, $C_1$-$C_{10}$, $C_1$-$C_8$, $C_1$-$C_6$, $C_1$-$C_5$, $C_1$-$C_4$, $C_1$-$C_3$, or $C_1$-$C_2$ alkyl groups. Examples of $C_1$-$C_{10}$ alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl groups, as well as their isomers. Examples of $C_1$-$C_4$-alkyl groups include, for example, methyl, ethyl, propyl, 1-methylethyl, butyl, 1-methylpropyl, 2-methylpropyl, and 1,1-dimethylethyl groups.

Cyclic alkyl groups or "cycloalkyl" groups include cycloalkyl groups having from 3 to 10 carbon atoms. Cycloalkyl groups can include a single ring, or multiple condensed rings. In some examples, cycloalkyl groups include $C_3$-$C_4$, $C_4$-$C_7$, $C_5$-$C_7$, $C_4$-$C_6$, or $C_5$-$C_6$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

Alkyl and cycloalkyl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999, hereby incorporated by reference.

Terms including the term "alkyl," such as "alkylamino" or "dialkylamino," will be understood to comprise an alkyl group as defined above linked to another functional group, where the group is linked to the compound through the last group listed, as understood by those of skill in the art.

The term "alkenyl," as used herein, refers to both straight and branched carbon chains which have at least one carbon-carbon double bond. In some examples, alkenyl groups can include $C_2$-$C_{20}$ alkenyl groups. In other examples, alkenyl can include $C_2$-$C_{12}$, $C_2$-$C_{10}$, $C_2$-$C_8$, $C_2$-$C_6$, or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups can include more than one double bond in the chain. The one or more unsaturations within the alkenyl group can be located at any position(s) within the carbon chain as valence permits. In some examples, when the alkenyl group is covalently bound to one or more additional moieties, the carbon atom(s) in the alkenyl group that are covalently bound to the one or more additional moieties are not part of a carbon-carbon double bond within the alkenyl group. Examples of alkenyl groups include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl groups.

The term "alkynyl," as used herein, refers to both straight and branched carbon chains which have at least one carbon-carbon triple bond. In one embodiment of alkynyl, the number of triple bonds is 1-3; in another embodiment of alkynyl, the number of triple bonds is one or two. In some examples, alkynyl groups include from $C_2$-$C_{20}$ alkynyl groups. In other examples, alkynyl groups can include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl, and 4-methylpent-2-yn-5-yl groups.

Alkenyl and alkynyl groups can be unsubstituted or substituted with one or more moieties chosen from alkyl, halo, haloalkyl, hydroxyl, carboxyl, acyl, acyloxy, amino, alkyl- or dialkylamino, amido, acylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999.

The term "aryl," as used herein, refers to a monovalent aromatic carbocyclic group of from 6 to 14 carbon atoms. Aryl groups can include a single ring or multiple condensed rings. In some examples, aryl groups include $C_6$-$C_{10}$ aryl groups. Aryl groups include, but are not limited to, phenyl, biphenyl, naphthyl, tetrahydronaphthyl, phenylcyclopropyl and indanyl. Aryl groups can be unsubstituted or substituted by one or more moieties chosen from halo, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkylsulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "alkylaryl," as used herein, refers to an aryl group that is bonded to a parent compound through a diradical alkylene bridge, ($-CH_2-$)$_n$, where n is 1-12 (e.g., n is from 1 to 6) and where "aryl" is as defined above. The term "arylalkyl," as used herein, refers to an aryl group, as defined above, which is substituted by an alkyl group, as defined above.

The term "alkylcycloalkyl," as used herein, refers to a cycloalkyl group that is bonded to a parent compound through a diradical alkylene bridge, ($-CH_2-$)$_n$, where n is 1-12 (e.g., n is from 1 to 6) and where "cycloalkyl" is as defined above.

The term "alkoxy," as used herein, refers to alkyl-O—, wherein alkyl refers to an alkyl group, as defined above. Similarly, the terms "alkenyloxy," "alkynyloxy," and "cycloalkoxy," refer to the groups alkenyl-O—, alkynyl-O—, and cycloalkyl-O—, respectively, wherein alkenyl, alkynyl, and cycloalkyl are as defined above. Examples of $C_1$-$C_6$-alkoxy groups include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

The term "alkylthio," as used herein, refers to alkyl-S—, wherein alkyl refers to an alkyl group, as defined above. Similarly, the term "cycloalkylthio," refers to cycloalkyl-S— where cycloalkyl are as defined above.

The term "alkylsulfinyl," as used herein, refers to alkyl-S(O)—, wherein alkyl refers to an alkyl group, as defined above.

The term "alkylsulfonyl," as used herein, refers to alkyl-S(O)$_2$—, wherein alkyl is as defined above.

The terms "alkylamino" and "dialkylamino," as used herein, refer to alkyl-NH— and (alkyl)$_2$N— groups, where alkyl is as defined above.

The terms "alkylcarbonyl," "alkoxycarbonyl," "alkylaminocarbonyl," and "dialkylaminocarbonyl," as used herein, refer to alkyl-C(O)—, alkoxy-C(O)—, alkylamino-C(O)— and dialkylamino-C(O)— respectively, where alkyl, alkoxy, alkylamino, and dialkylamino are as defined above.

The term "heteroaryl," as used herein, refers to a monovalent aromatic group of from 1 to 15 carbon atoms (e.g., from 1 to 10 carbon atoms, from 2 to 8 carbon atoms, from 3 to 6 carbon atoms, or from 4 to 6 carbon atoms) having one or more heteroatoms within the ring. The heteroaryl group can include from 1 to 4 heteroatoms, from 1 to 3 heteroatoms, or from 1 to 2 heteroatoms. In some examples, the heteroatom(s) incorporated into the ring are oxygen, nitrogen, sulfur, or combinations thereof. When present, the nitrogen and sulfur heteroatoms can optionally be oxidized. Heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings can be unsubstituted or substituted by one or more moieties as described for aryl above.

The term "alkylheteroaryl," as used herein, refers to a heteroaryl group that is bonded to a parent compound through a diradical alkylene bridge, (—CH$_2$—)$_n$, where n is 1-12 and where "heteroaryl" is as defined above.

The terms "heterocyclyl," "heterocyclic" and "heterocyclo" are used herein interchangeably, and refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, having one or more heteroatoms within the ring. The heterocyclyl group can include from 1 to 4 heteroatoms, from 1 to 3 heteroatoms, or from 1 to 2 heteroatoms. In some examples, the heteroatom(s) incorporated into the ring are oxygen, nitrogen, sulfur, or combinations thereof. When present, the nitrogen and sulfur heteroatoms can optionally be oxidized, and the nitrogen heteroatoms can optionally be quaternized. The heterocyclyl group can be attached at any heteroatom or carbon atom of the ring or ring system and can be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

The term "alkylheterocyclyl," as used herein, refers to a heterocyclyl group that is bonded to a parent compound through a diradical alkylene bridge, (—CH$_2$—)$_n$, where n is 1-12 and where "heterocyclyl" is as defined above. The term "heterocyclylalkyl," as used herein, refers to a heterocyclyl group, as defined above, which is substituted by an alkyl group, as defined above.

Heterocyclyl and heteroaryl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999

The term "halogen," as used herein, refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl (—CH$_2$Cl), dichloromethyl (—CHCl$_2$), trichloromethyl (—CCl$_3$)).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compositions and Methods

Compositions and methods for inhibits the binding of GTP to oncogenic mutant KRas are disclosed. These compositions may be used in method to treat a subject with cancer. In particular, the compositions may be used to treat cancers involving overactive Ras signaling.

In some embodiments, methods can involve administering an effective amount of a compound defined by Formula I below

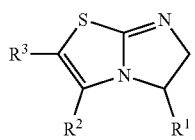

Formula I wherein
  $R^1$ is H, F, Cl, Br, $CF_3$, or an alkyl group or alkenyl group, optionally substituted with amino, amido, alkyl, alkenyl, alkynyl, alkoxyl, aryl, carbonyl, carboxylate, carbamyl, cyano, ester, guanidinyl, halogen, haloalkyl, heteroaryl, hydroxyl, nitrile, nitro, sulfinyl, sulfanyl, thiol, ureylene, or ureido;
  $R^2$ is an alkyl group, an alkenyl group, an alkynyl group, a cycloalkyl group, a heterocyclyl group, an aryl group, a heteroaryl group, optionally substituted with amino, amido, alkyl, alkenyl, alkynyl, alkoxyl, aryl, carbonyl, carboxylate, carbamyl, cyano, ester, guanidinyl, halogen, haloalkyl, heteroaryl, hydroxyl, nitrile, nitro, sulfinyl, sulfanyl, thiol, ureylene, or ureido, or —$CH_2$—$R^4$;
  $R^3$ is H, F, Cl, Br, $CF_3$, an alkyl group, or an alkenyl group;
  $R^4$ is an aryl group, an alkylaryl group, an arylalkyl group, a cycloalkyl group, an alkylcycloalkyl group, a heterocyclyl group, an alkylheterocyclyl group, a heteroaryl group, an alkylheteroaryl group, an alkoxy group, or an alkylthio group optionally substituted with amino, amido, alkyl, alkenyl, alkynyl, alkoxyl, aryl, carbonyl, carboxylate, carbamyl, cyano, ester, guanidinyl, halogen, haloalkyl, heteroaryl, hydroxyl, nitrile, nitro, sulfinyl, sulfanyl, thiol, ureylene, or ureido;
  or a pharmaceutical acceptable salt thereof, and optionally a pharmaceutically acceptable carrier.

In specific examples, the disclosed compounds have $R^3$ as alkyl, e.g., C1-8 alkyl, more specifically, $C_{1-4}$ alkyl, more specifically methyl.

In specific examples, the disclosed compounds can have R2 as unsubstituted phenyl or phenyl substituted In certain aspects, the disclosed compounds can have Formula IA, which is a subgenus of Formula I where $R^3$ is methyl and $R^2$ is phenyl.

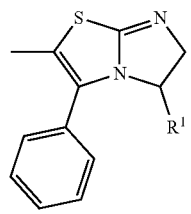

Formula IA wherein $R^1$ is as defined above. In specific examples, $R^1$ can be unsubstituted $C_{1-4}$ alkyl, for example isopropyl, or $C_{1-4}$ alkyl substituted with hydroxyl, guanidinyl, phenyl (i.e., benzyl), phenol, tolyl, or heteroaryl.

In other aspects, the disclosed compounds can have Formula IB, which is a subgenus of Formula I where $R^3$ is hydrogen and $R^2$ is substituted or unsubstituted phenyl and $R^1$ is as defined above.

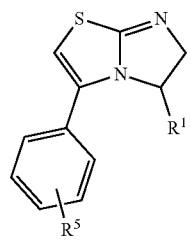

Formula IB wherein $R^5$ is hydrogen amino, amido, alkyl, alkenyl, alkynyl, alkoxyl, aryl, carbonyl, carboxylate, carbamyl, cyano, ester, guanidinyl, halogen, haloalkyl, heteroaryl, hydroxyl, nitrile, nitro, sulfinyl, sulfanyl, thiol, ureylene, or ureido, or —$CH_2$—$R^4$. In specific examples, $R^1$ can be unsubstituted $C_{1-4}$ alkyl, for example isopropyl, or $C_{1-4}$ alkyl substituted with hydroxyl, guanidinyl, phenyl (i.e., benzyl), phenol, tolyl, or heteroaryl.

In certain embodiments, the compound can be

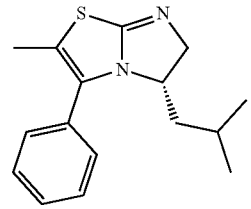

In certain embodiments, the compound can be

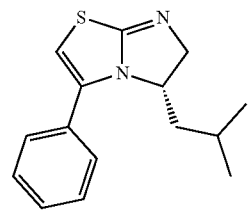

Figure 4:
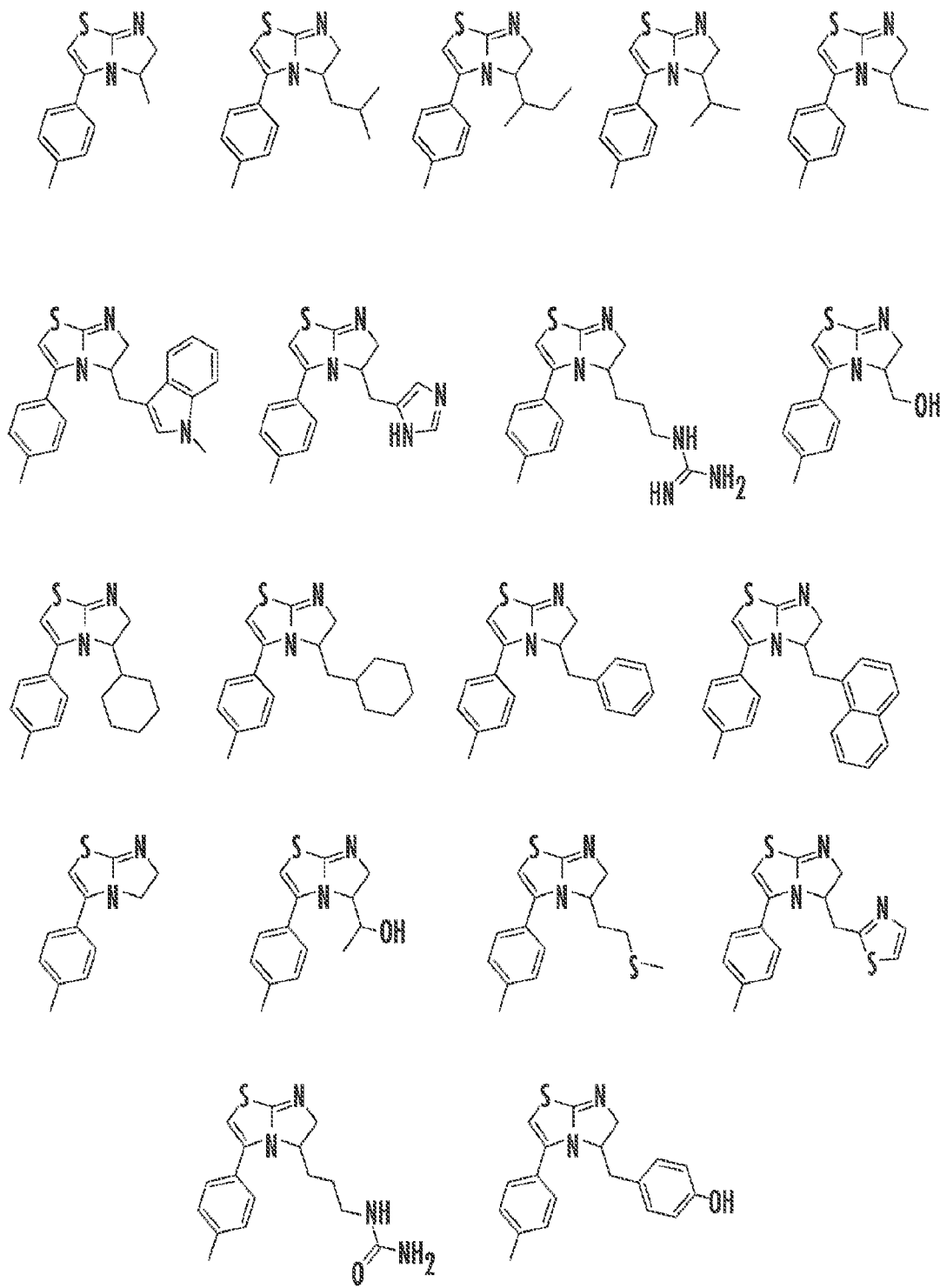
FIG. 4 is a group of chemical structures of compounds as disclosed herein.
Figure 5:
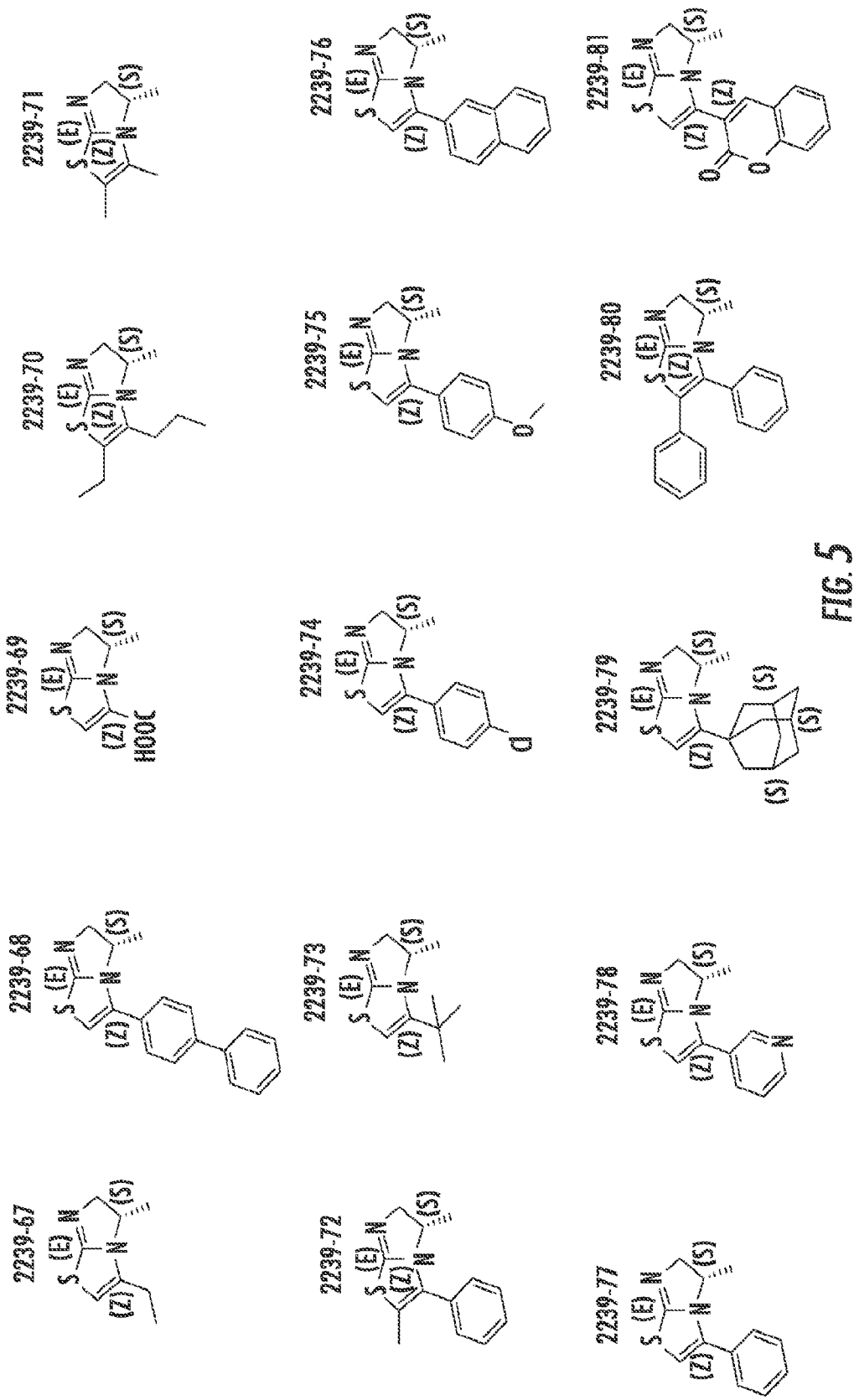
FIG. 5 is a group of chemical structures of compounds as disclosed herein.
Figure 5:
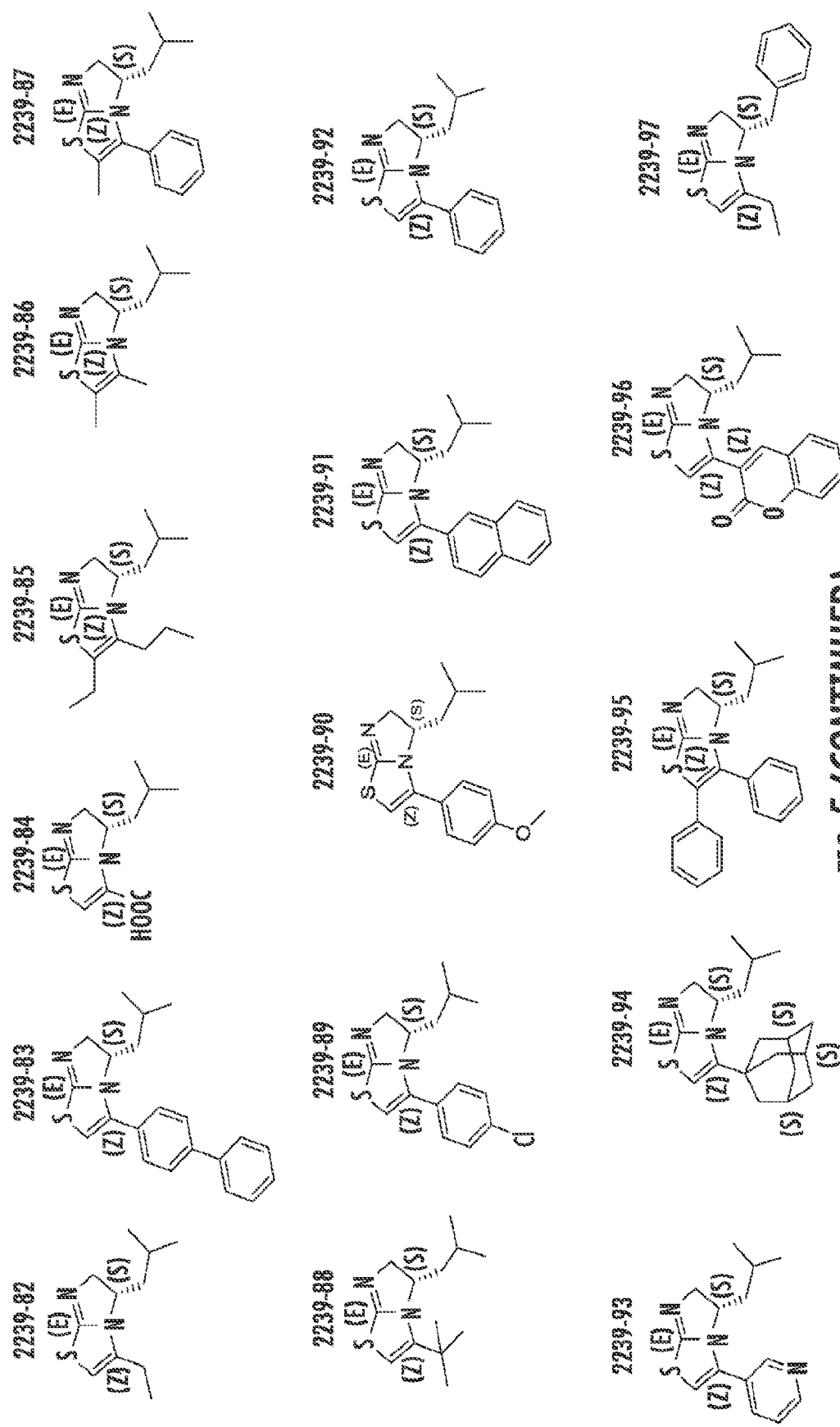
Figure 5:
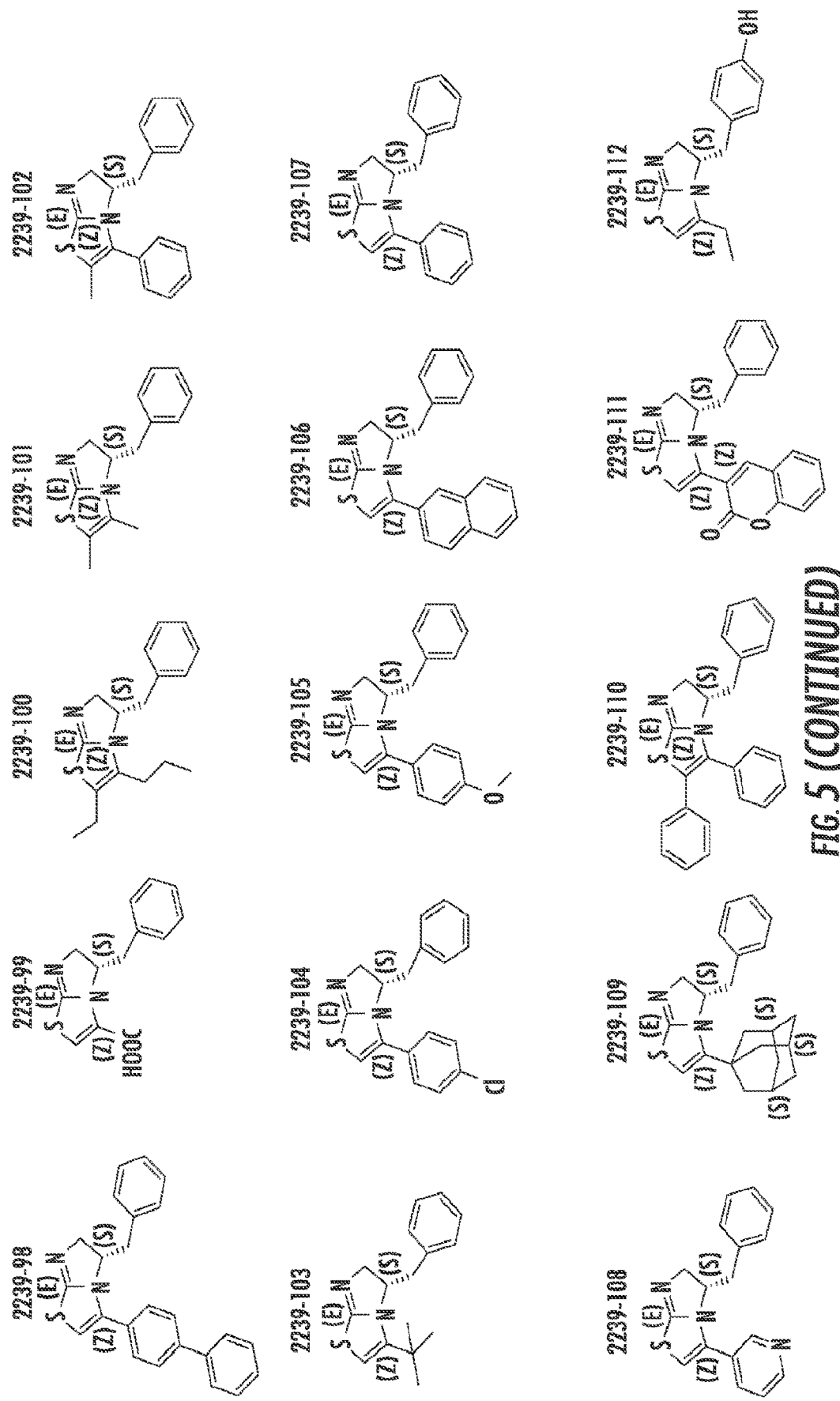
Figure 5:
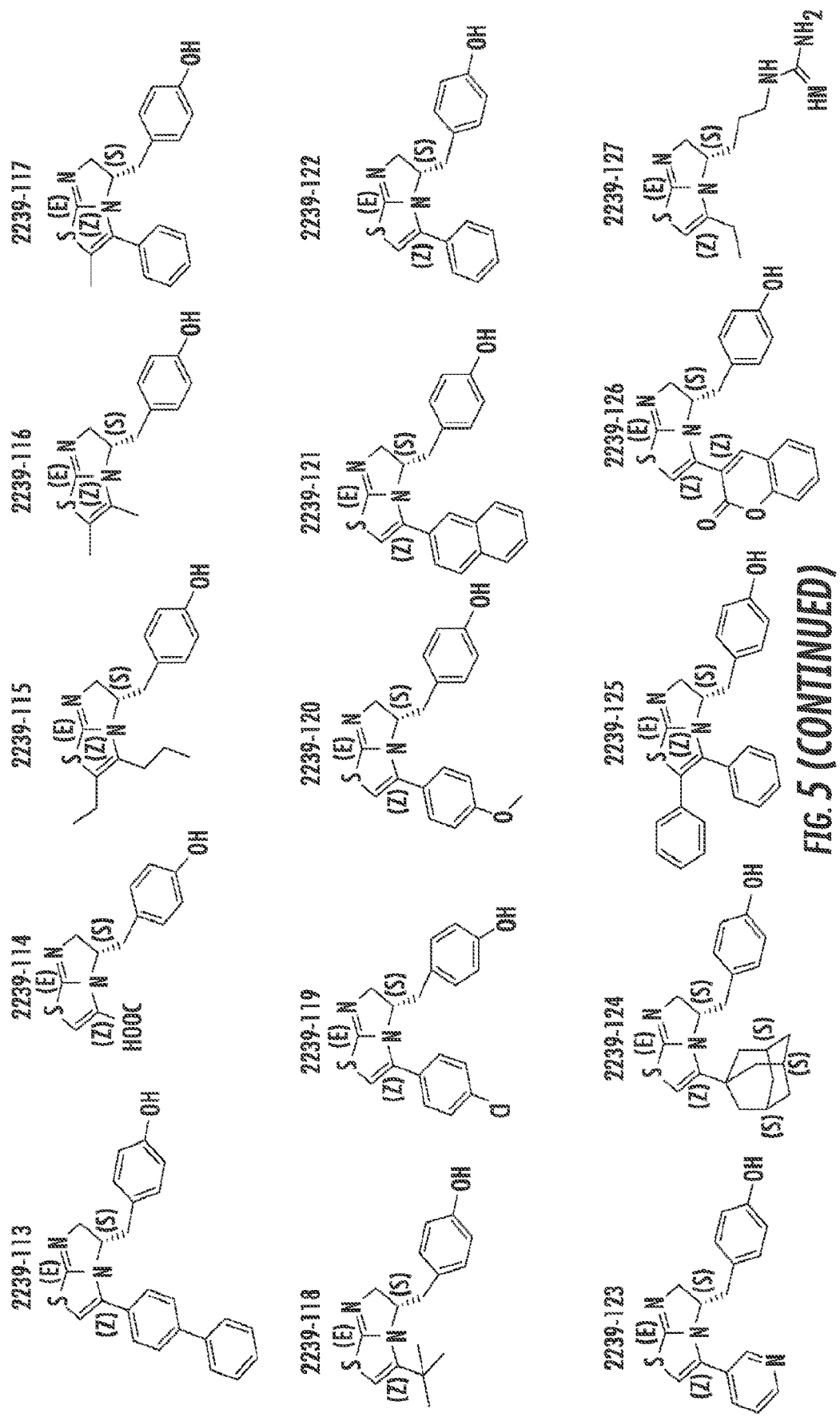
Figure 5:
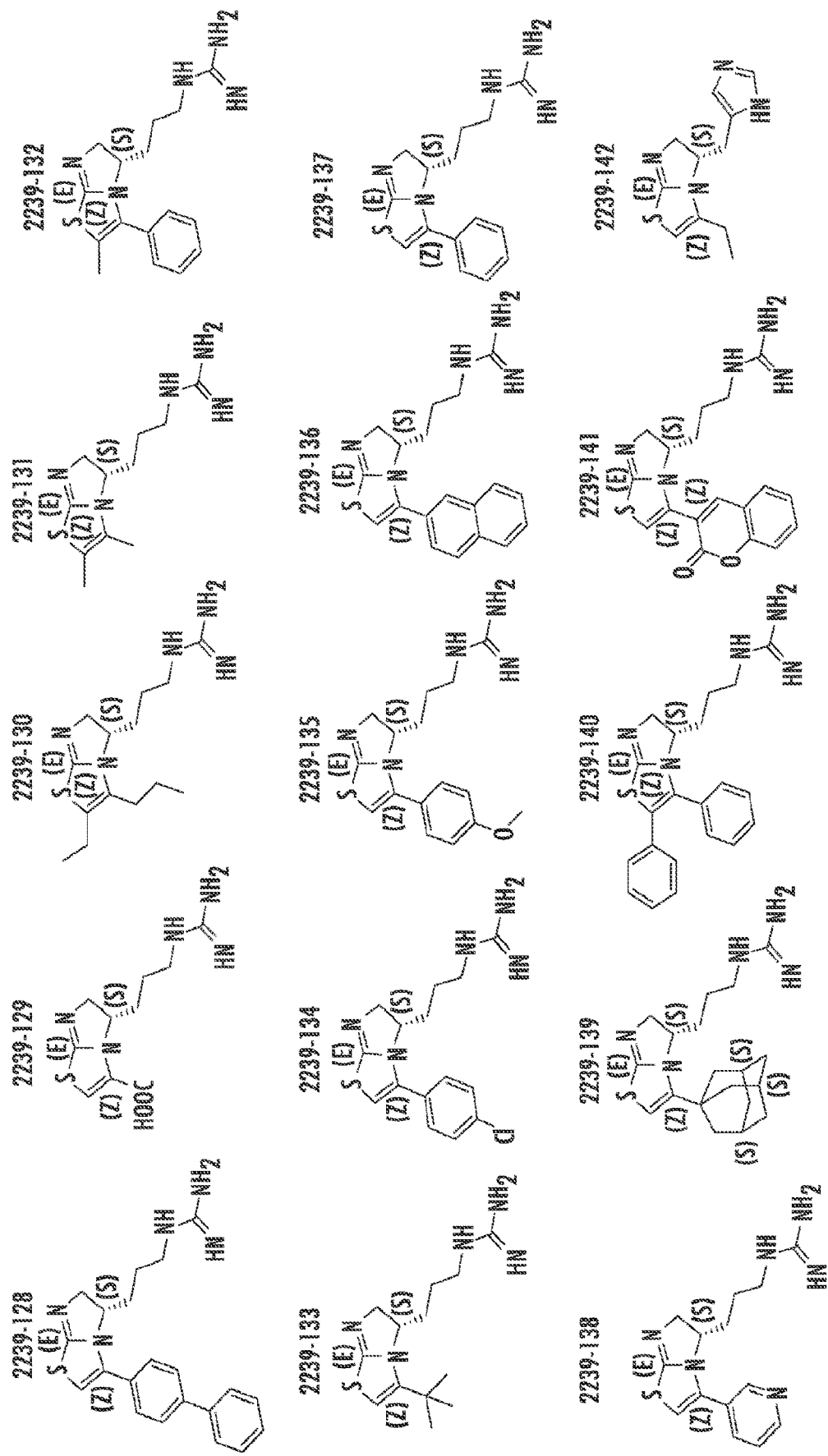
Figure 5:
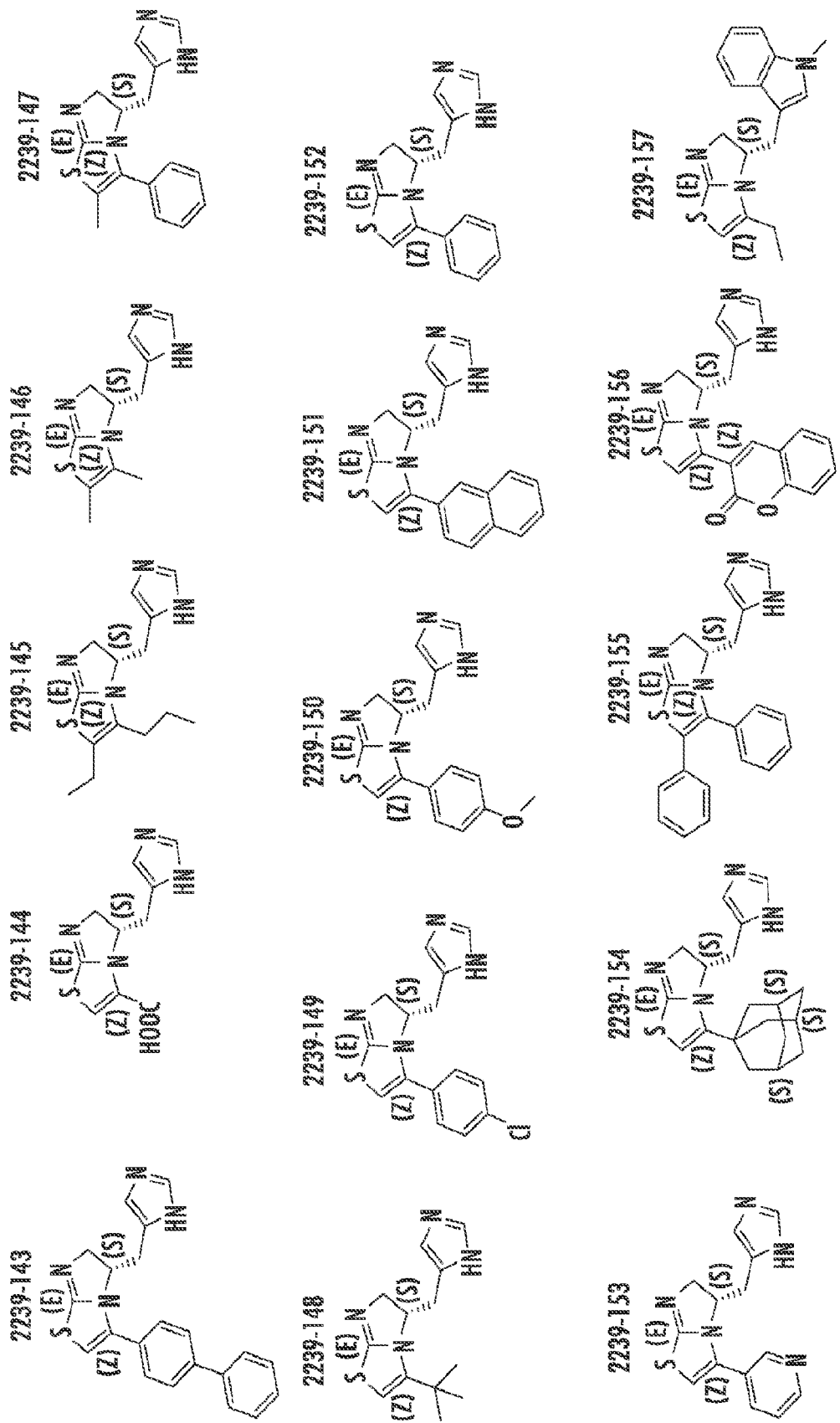
Figure 5:
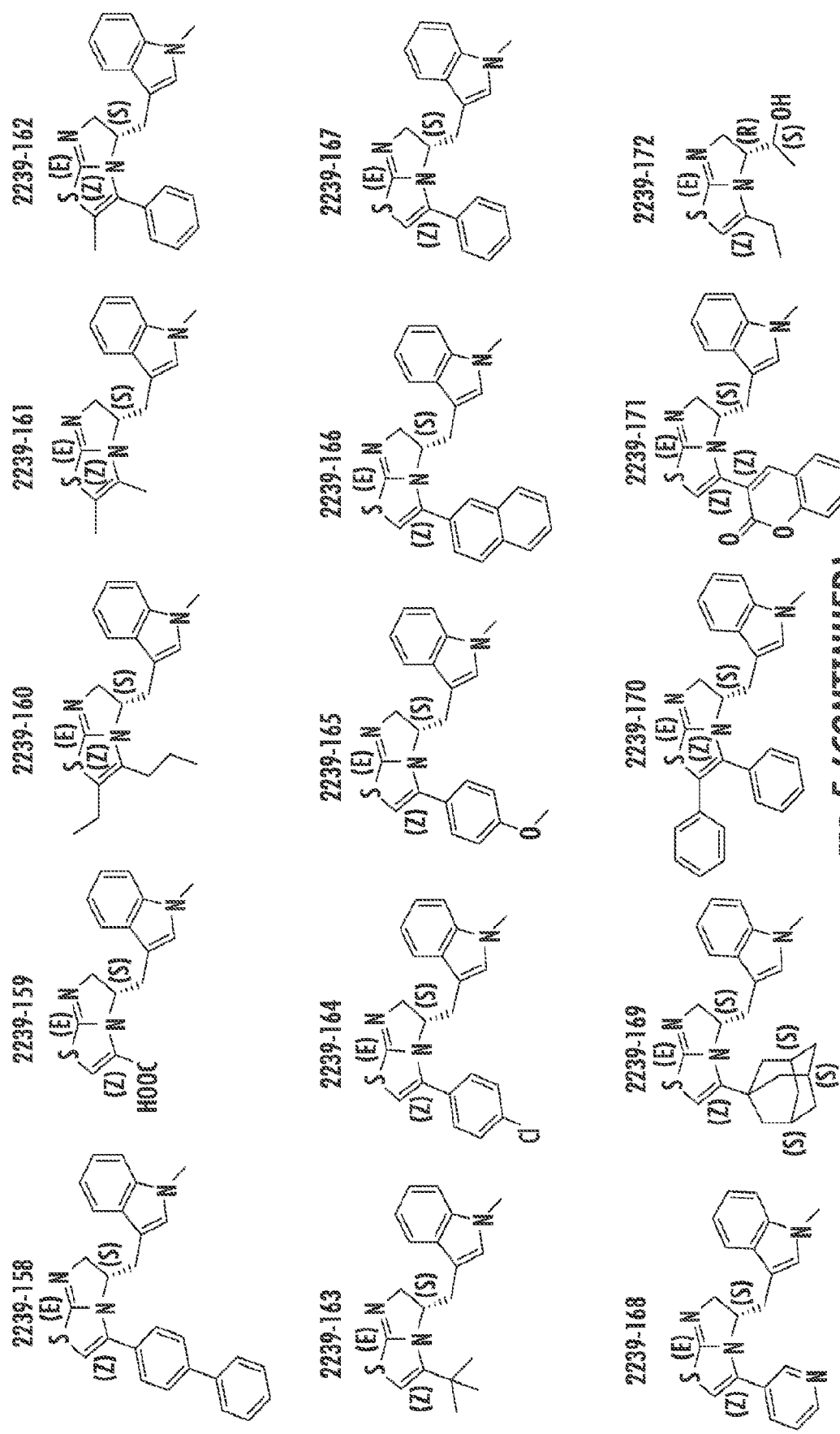
Figure 5:
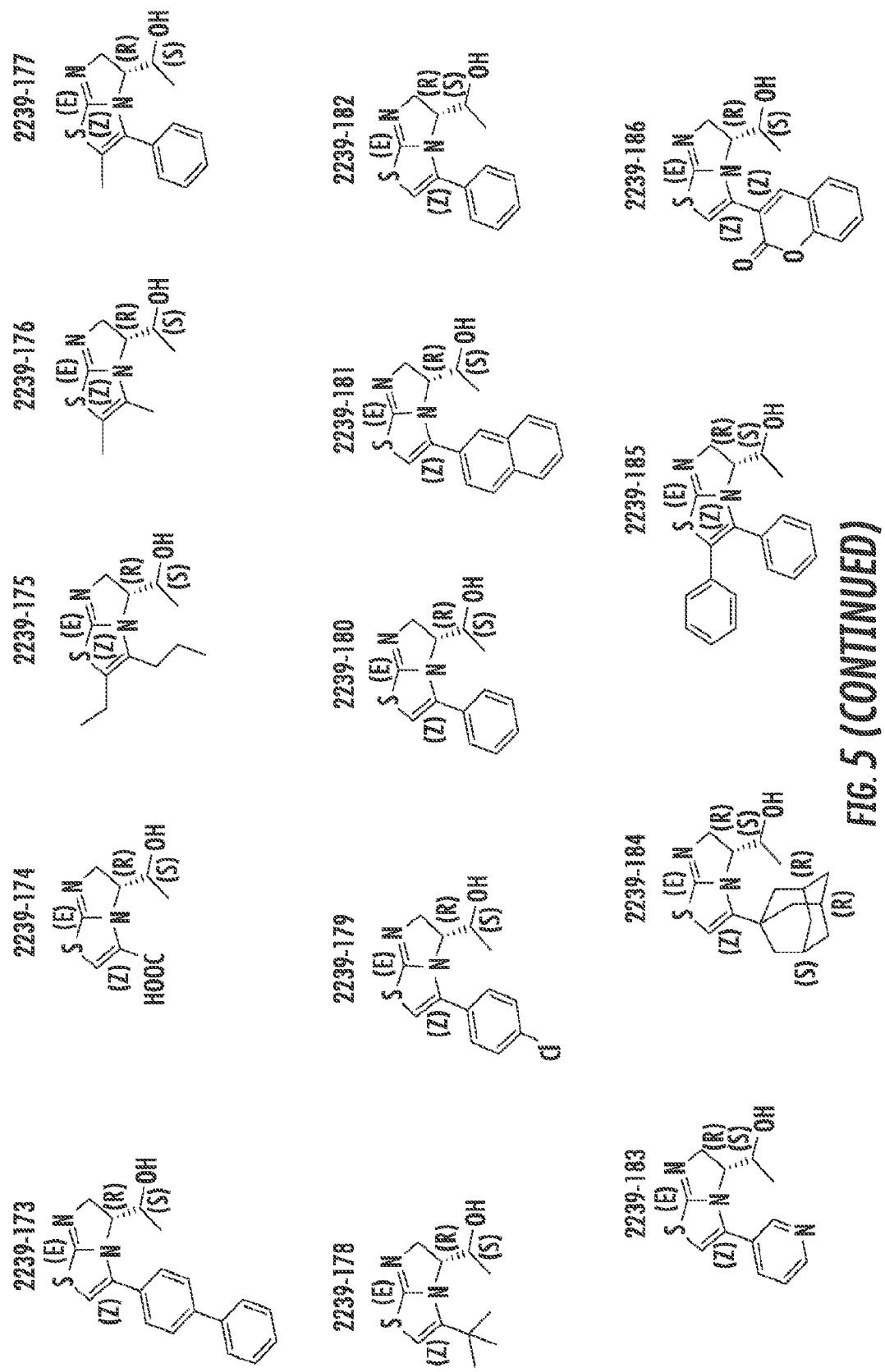
Figure 5:
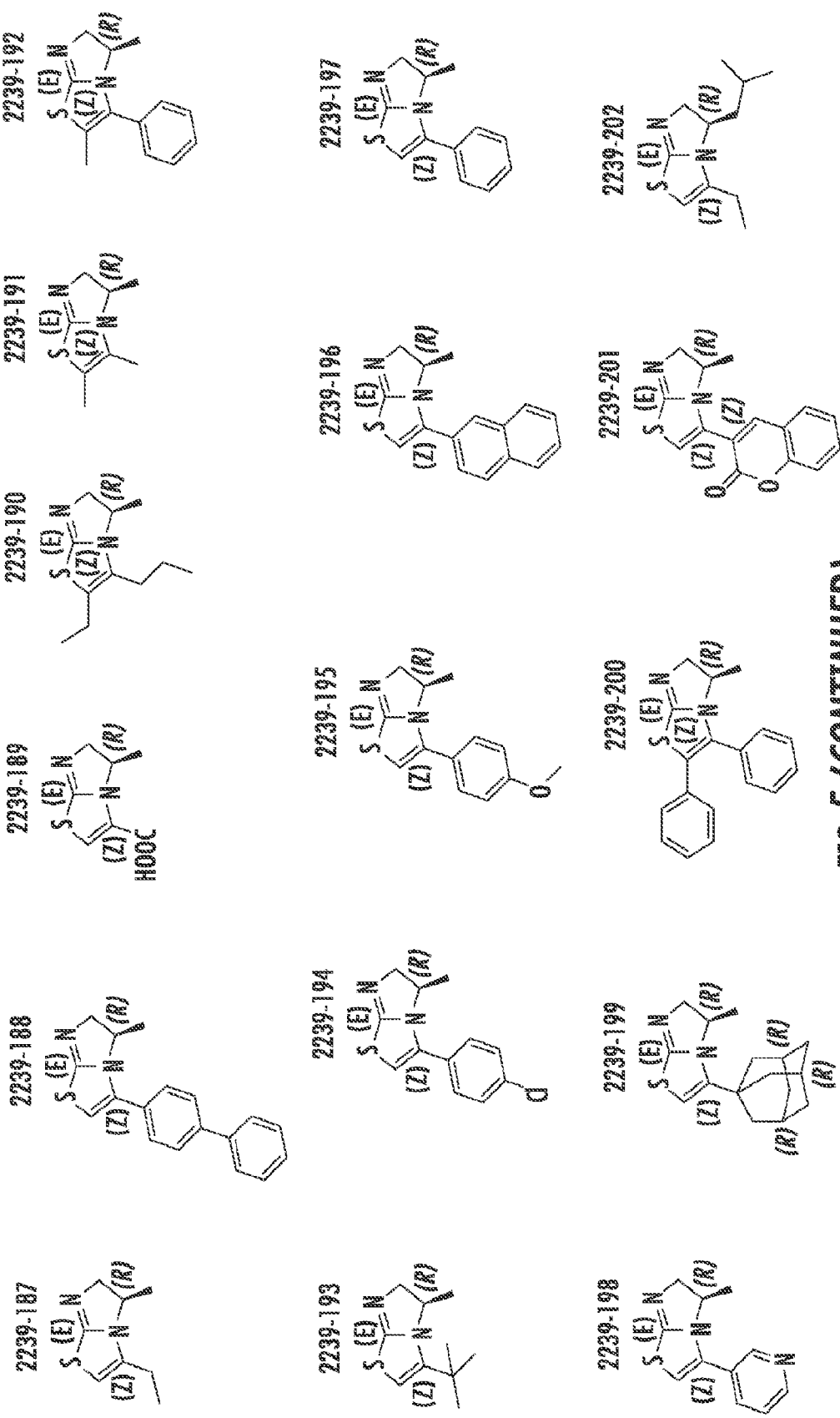
Figure 5:
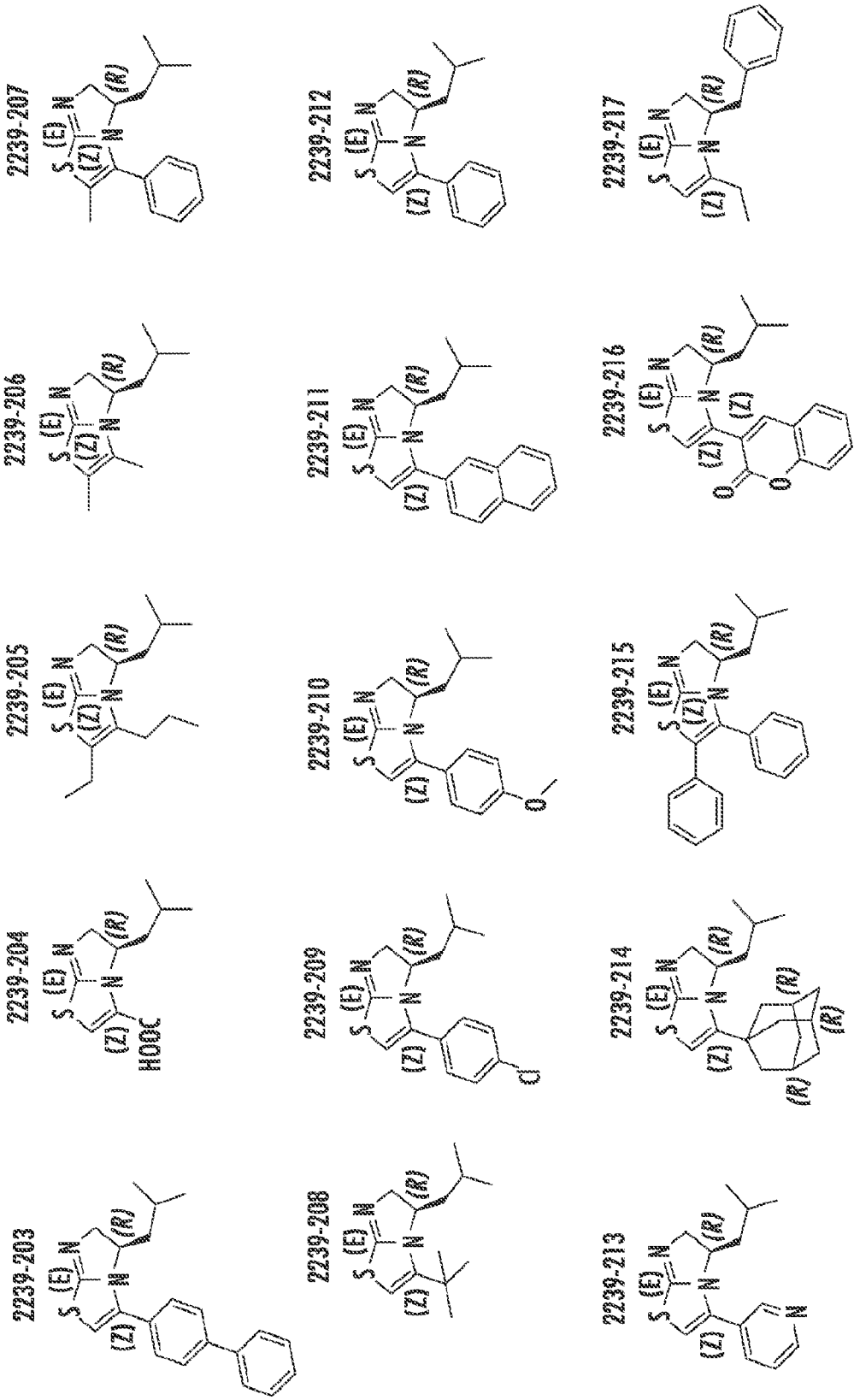
Figure 5:
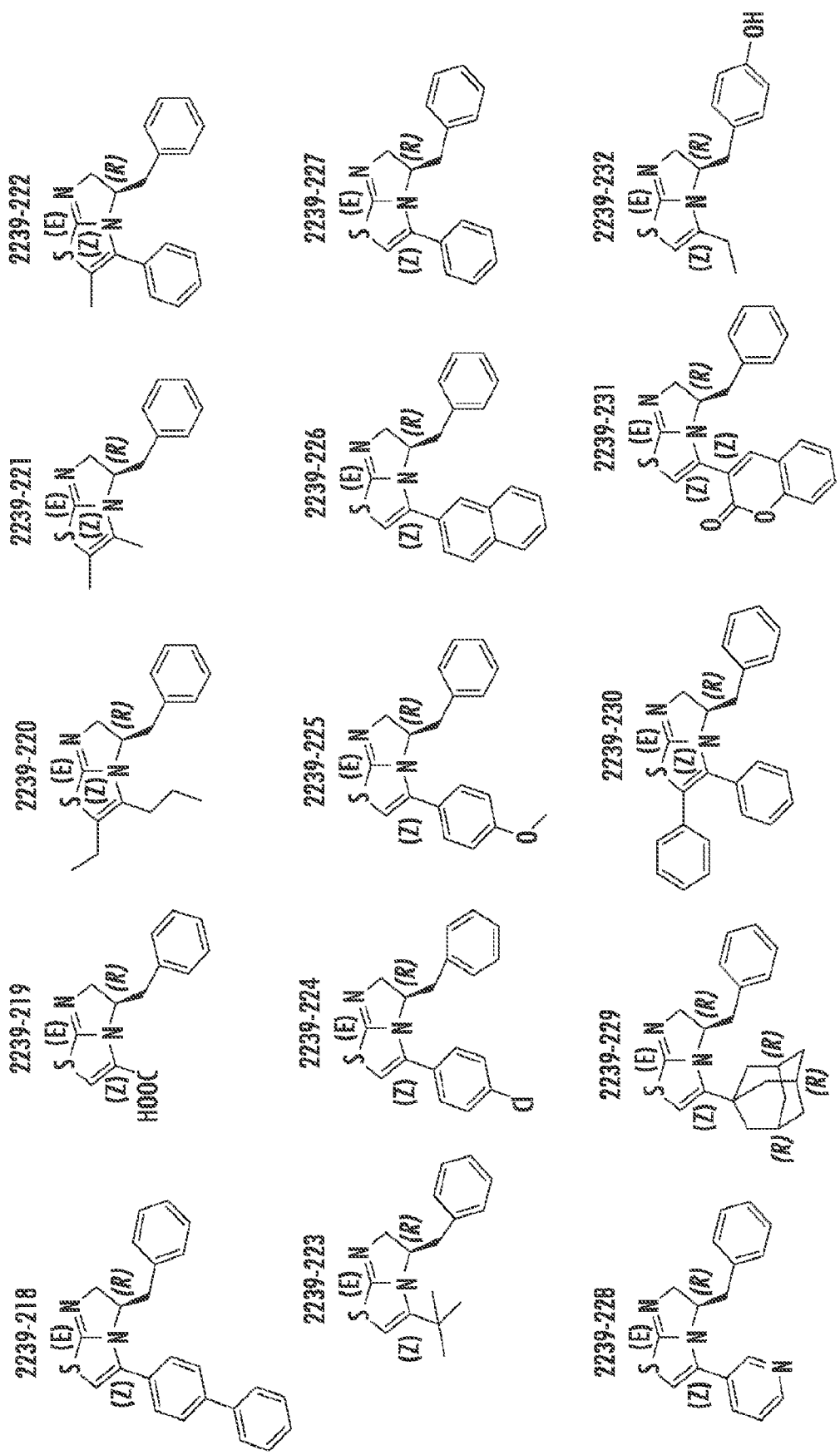
Figure 5:
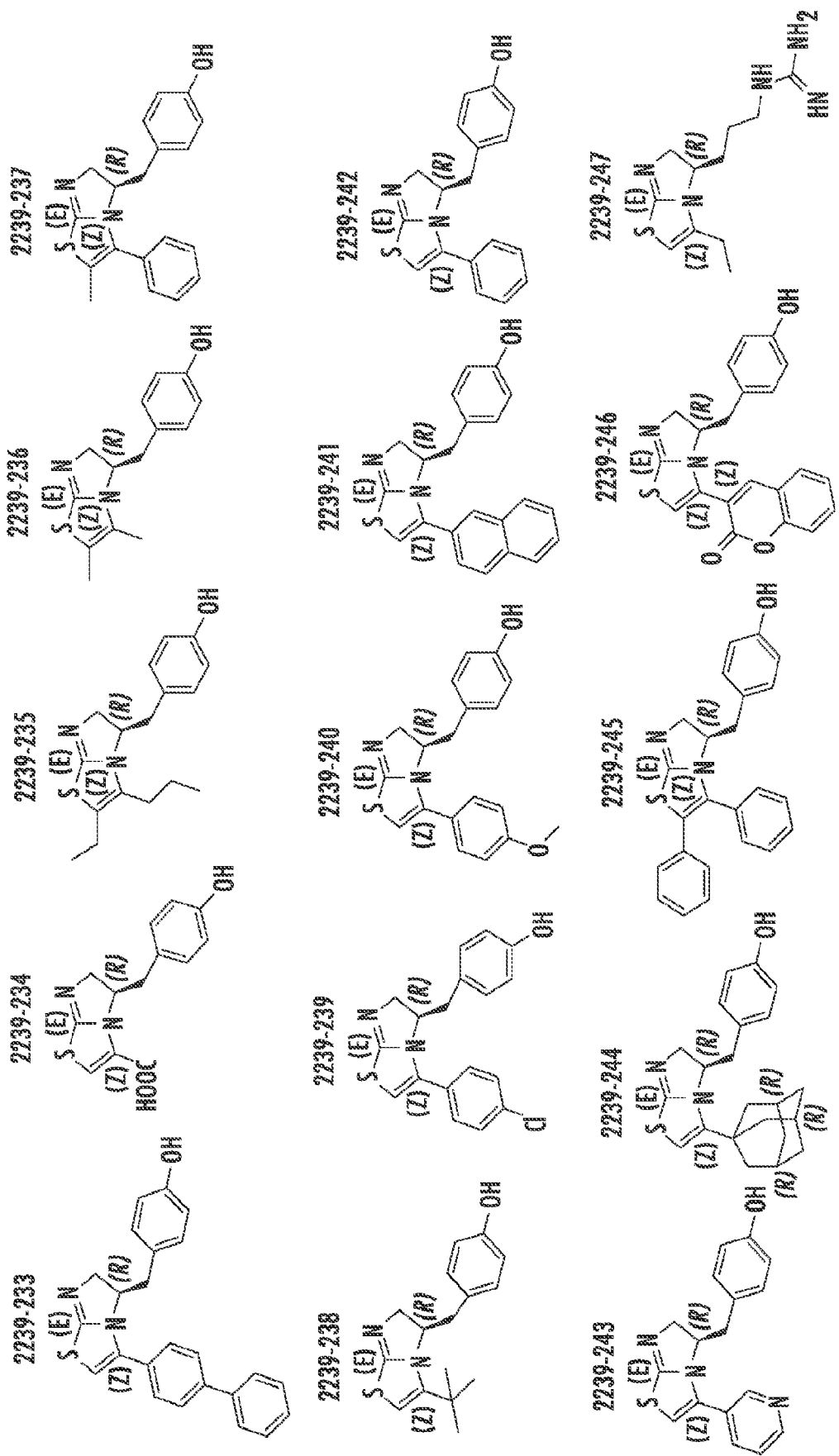
Figure 5:
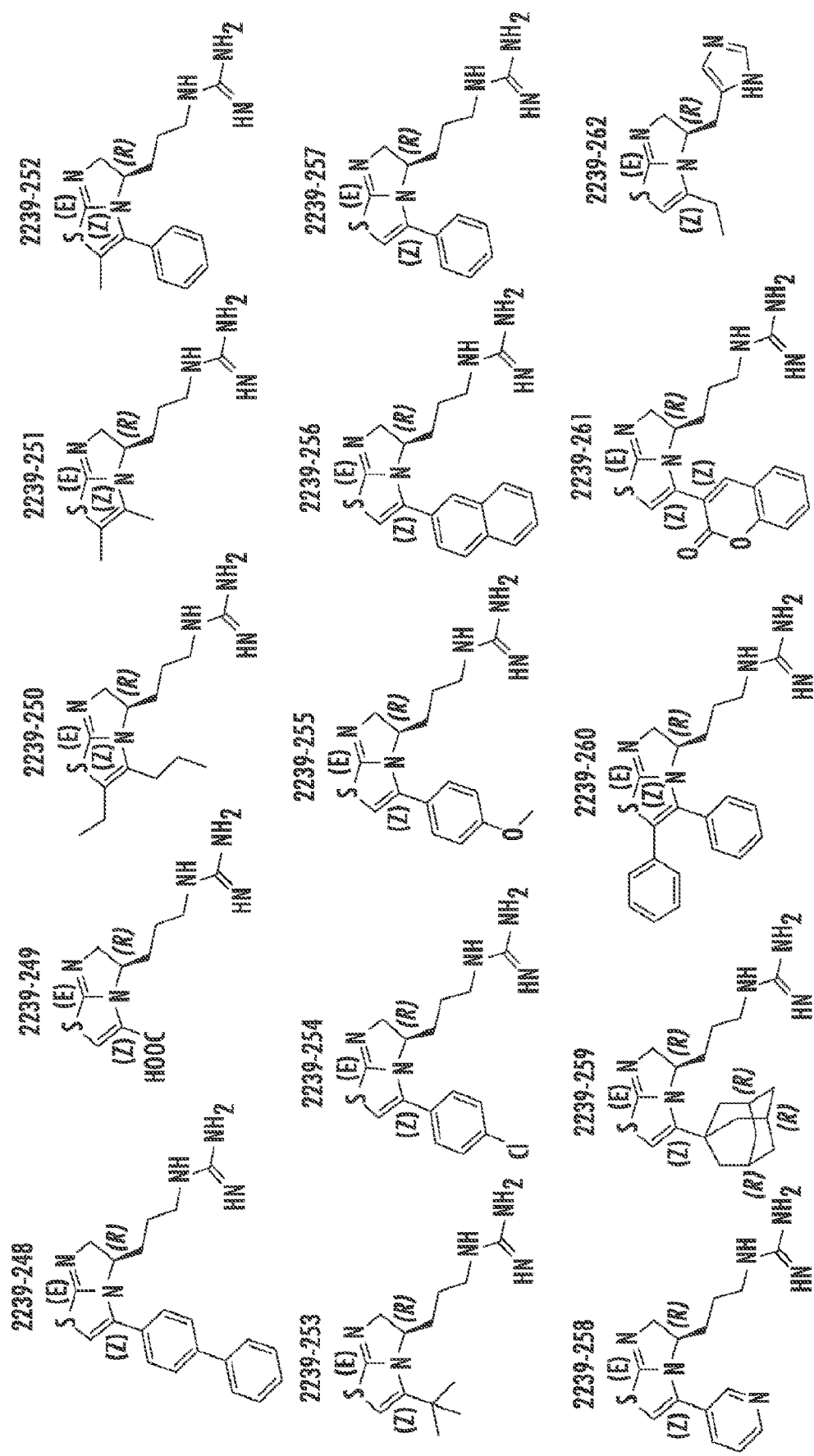
Figure 5:
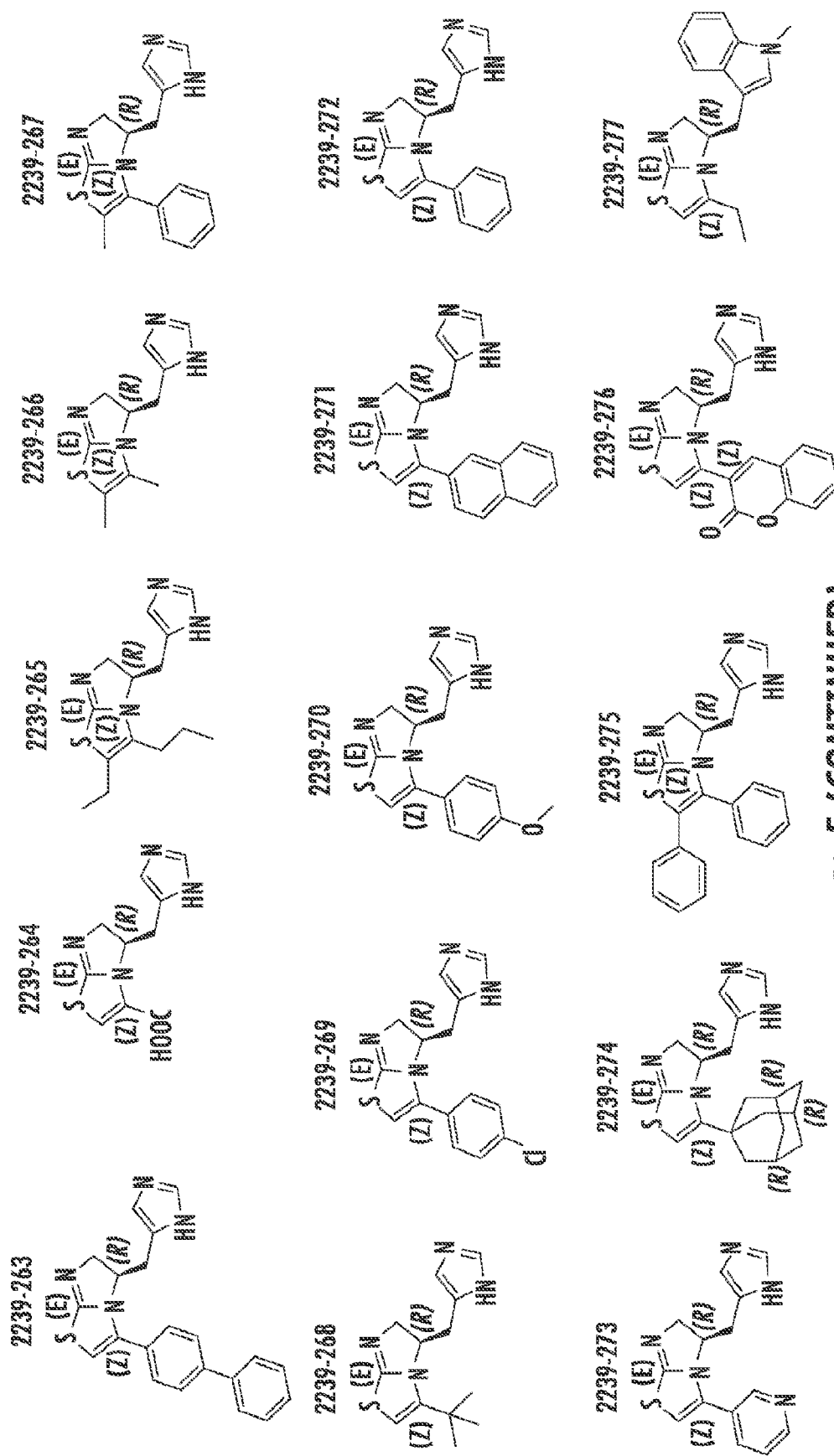
Figure 5:
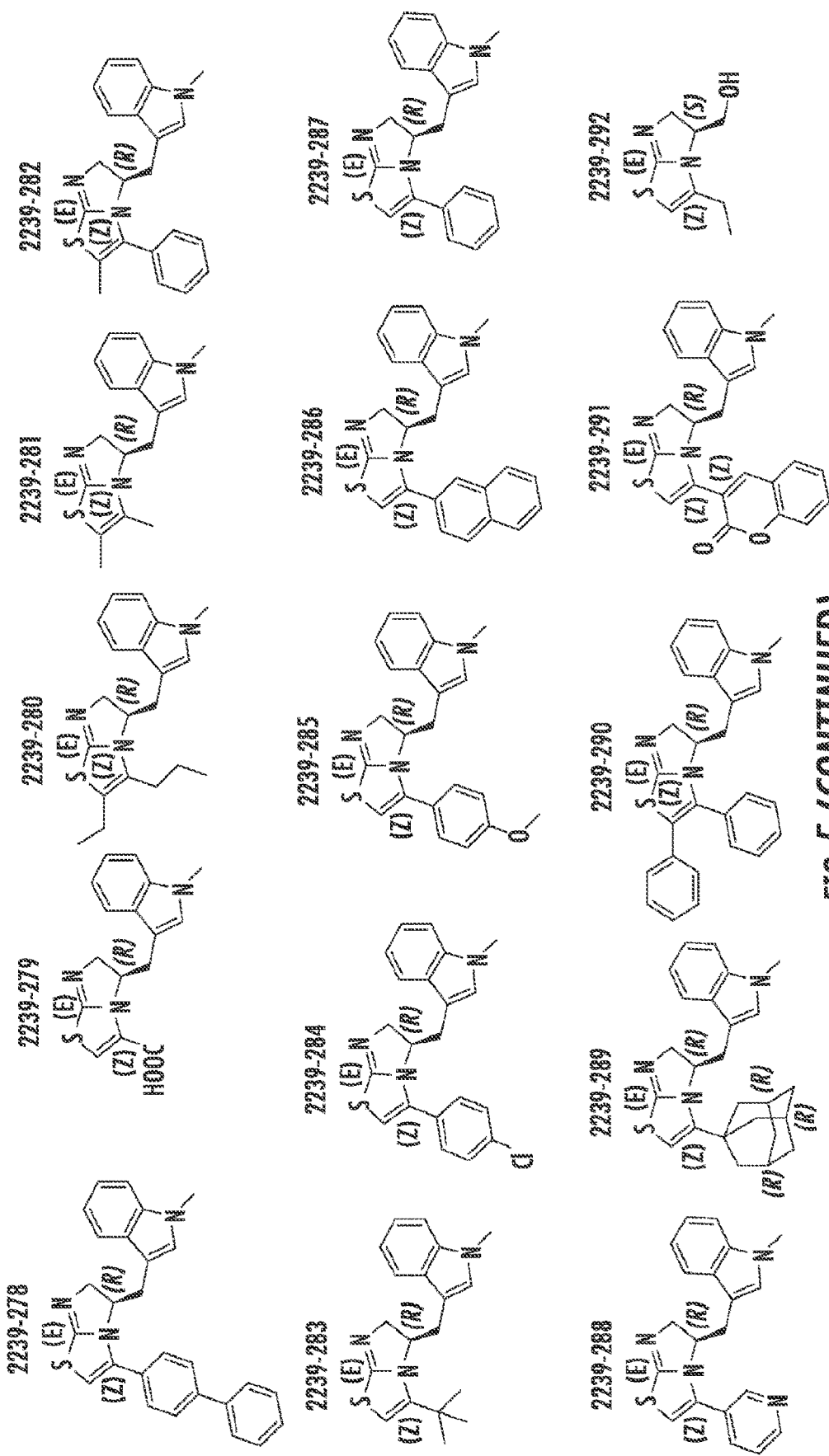
Figure 5:
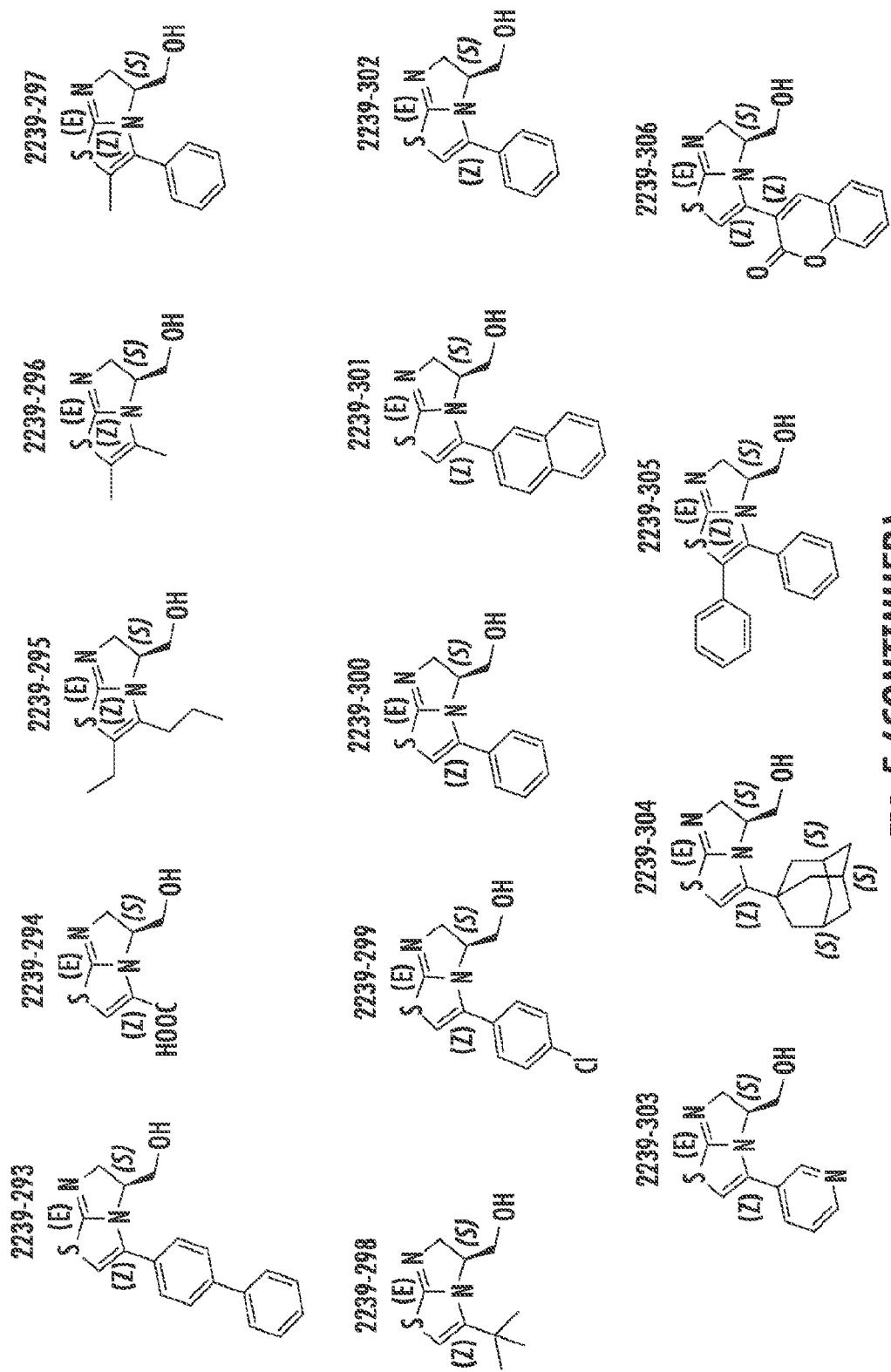
Figure 6:
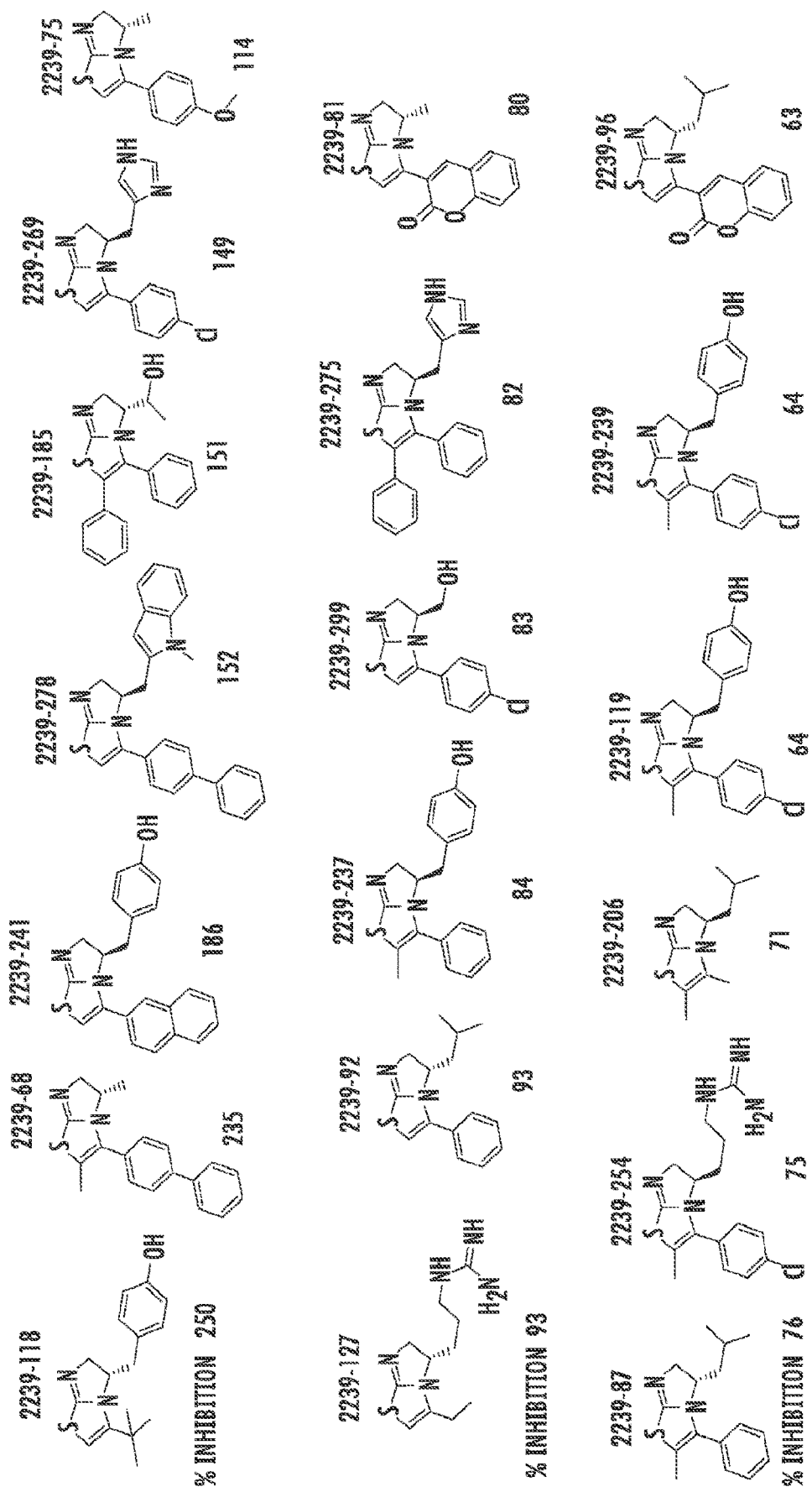
FIG. 6 is a group of chemical structures of compounds with their percent inhibition.

Other specific examples of compounds of Formulas I, IA, and IBA are shown in FIG. 4, FIG. 5, and FIG. 6. Pharmaceutically acceptable salts of these compounds are also contemplated herein as are such compounds with a pharmaceutically acceptable carrier.

Also provided are pharmaceutical compositions comprising a therapeutically effective amount of one or more of these compounds and a pharmaceutically acceptable excipient.

A number of embodiments of the invention have been described. Nevertheless, it will be understood that various modifications may be made without departing from the spirit and scope of the invention. Accordingly, other embodiments are within the scope of the following claims.

Methods of Use

Further provided herein are methods of treating or preventing cancer in a subject, comprising administering to the subject an effective amount of a compound or composition as disclosed herein. Additionally, the method can further comprise administering an effective amount of ionizing radiation to the subject and/or another anti-cancer compound. Also disclosed are methods of imaging a cancer cell comprising contacting the cell with a compound as disclosed herein.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor. In a preferred aspect, the cancer is pancreatic cancer.

Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

The disclosed subject matter also concerns a packaged dosage formulation comprising in one or more containers at least one inhibitor compound or composition disclosed herein, e.g., any compound of Formulas I. A packaged dosage formulation can optionally comprise in one or more containers a pharmaceutically acceptable carrier or diluent. A packaged dosage formulation can also optionally comprise, in addition to an inhibitor compound or composition disclosed herein, other GTP inhibitors, or an immunotherapeutic such as ipilimumab.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Ras activation is catalyzed by GEFs such as SOS that exchange bound GDP for GTP, whereas Ras inactivation is catalyzed by GAPs leading to the hydrolysis of GTP to GDP. Oncogenic mutations in KRas impair GTP hydrolysis, leading to a constitutively activated, GTP-bound mt KRas, which contributes significantly to human cancer pathogenesis and patient tumor resistance. The purpose of this example is to identify small molecules that bind mt KRas directly and shift its state from GTP to GDP, inhibiting its ability to bind its effectors. Although the picomolar affinity for GTP and the difficulty in identifying allosteric sites have made it hard to target directly Ras, evidence for the feasibility of targeting Ras has been reported. Recently, one report provided compelling evidence of small molecules that can bind covalently to Cys, occupy a pocket composed largely of the switch II region of G12C mt KRas, and inhibit the interaction of Ras-GTP with its effectors. Other recent reports identified small molecules that inhibited SOS-mediated nucleotide exchange by binding to a pocket adjacent to the switch I/II regions of KRas. Although compounds that exclusively inhibit GDP exchange for GTP may be effective in tumors that depend on wt Ras for their malignancy, they are less likely to affect tumors with mt GTP-bound Ras.

Results

Assay 1: The Mant-GDP assay was used to identify compounds that inhibit the ability of GTP to bind mt G12D KRas and to displace fluorescently labeled mant-GDP (29-deoxy-39-O—(N-methylanthraniloyl-GDP). Briefly, the assay consists of incubating purified mt KRas protein with mant-GDP, with a reference fluorescence measurement taken when mant-GDP is bound to KRas. The addition of non-labeled GTP causes a binding competition and displacement of mant-GDP from mt KRas, resulting in a lowered fluorescence signal. Compounds that prevent this decrease in fluorescence signal in the presence of non-labeled GTP may demonstrate allosteric inhibition of the ability of GTP to bind mt KRas. Optimization of this assay showed that both GTP and GDP were very effective at displacing mant-GDP from mt G12D KRas, with a slight preference for GTP (FIG. 1A), as reported previously for mt G12C KRas.

Figure 1B:
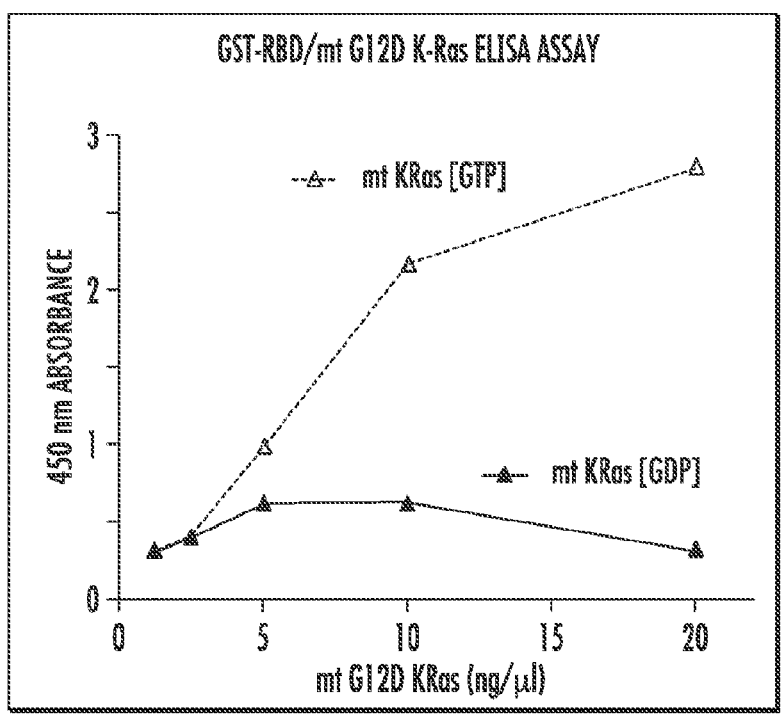

Assay 2: The GST-RBD ELISA assay was used to identify compounds that inhibit the binding of mt KRas to the Ras binding domain (RBD) of its effector Raf-1. This assay was adapted from an established ELISA assay. Briefly, the assay consists of first loading mt G12D KRas with 100 µM GTP or GDP in TBS buffer (25 mM Tris, 0.15M NaCl, pH 7.4) and 10 mM EDTA, followed by 60 mM MgCl2, then diluting mt KRas in binding buffer (2 mM $MgCl_2$, 10 mM $Na_2CO_3$, 30 mM $NaHCO_3$, pH 9.6) prior to incubating in a 96-well plate overnight. After blocking and washing, GST-RBD was added (compounds can also be added at this step), followed by HRP-conjugated anti-GST antibody and then by TMB substrate and reading the absorbance at 450 nm. Optimization of this assay showed that GST-RBD binds with higher affinity to GTP-versus GDP-bound mt G12D KRas (FIG. 1B).

Chemical Library: The Torrey Pines Institute for Molecular Studies (TPIMS) library, a mixture-based synthetic combinatorial library containing over 6 million compounds prepared as 62 mixtures varying in size between 1,000 and 800,000 compounds per mixture, was screened. The 62 mixtures are referred to as the "scaffold ranking library" since each mixture sample contains only compounds with the same specific core scaffold with close structural analogs. Hits identified from the scaffold ranking library were deconvoluted through subsequent screens of the corresponding positional scanning libraries, and based on the data generated from these libraries, 20 to 50 individual compounds were selected, synthesized, and evaluated. This is a highly innovative approach to scan a rich chemical space of over 6 million compounds by screening only 100s to 1000s of wells. The highly diverse and dense chemical space that the TPIMS library occupies coupled with its outstanding drug-like properties led to its extensive use to identify activity cliffs and unique leads for optimization for preclinical and clinical studies.

Figure 2:
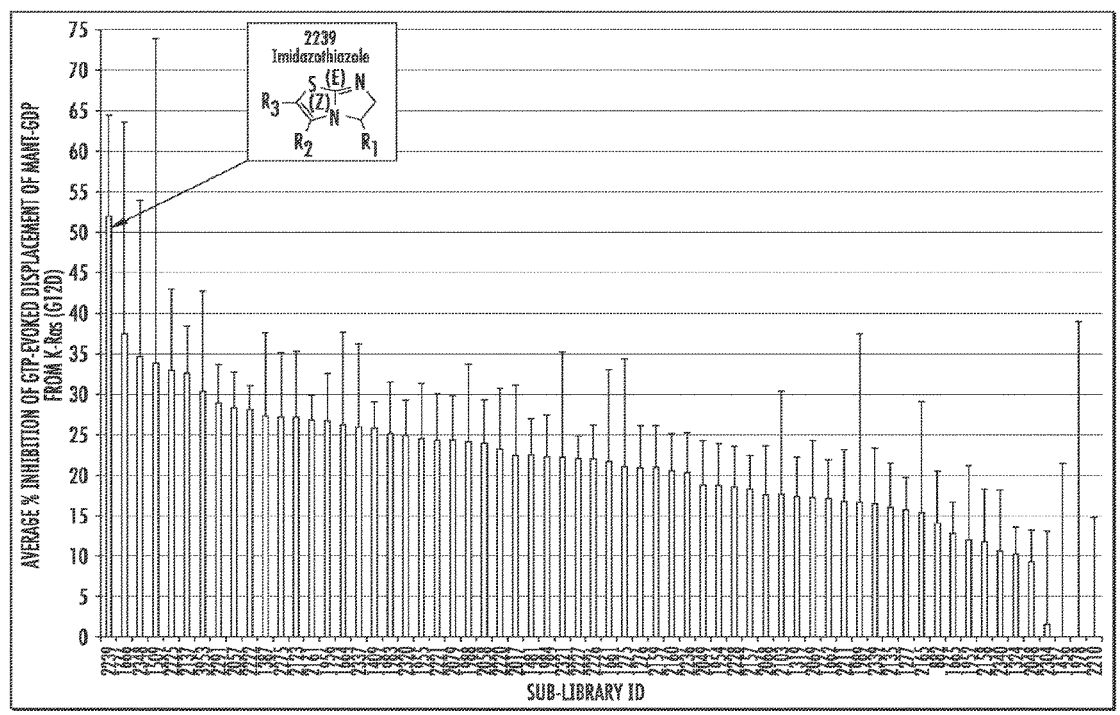
FIG. 2 shows screening TPIMS scaffold ranking library identified hits that inhibited GTP from displacing mant-GDP from mtG12DKras. The most potent 2239 mixture was de-convoluted through positional scanning libraries.
Figure 3A:
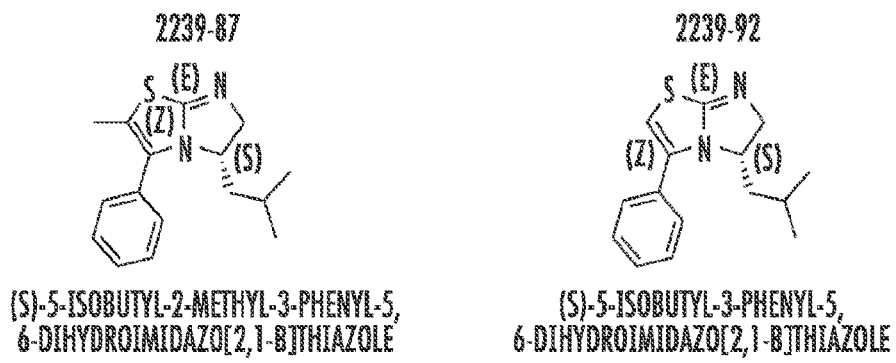
FIG. 3A, FIG. 3B, and FIG. 3C show screening the TPIMS scaffold ranking library and subsequent de-convolution through positional scanning libraries led to the identification of 2239-87 which inhibits the ability of GTP to displace mant-GDP from mt G12D.
Figure 3B:
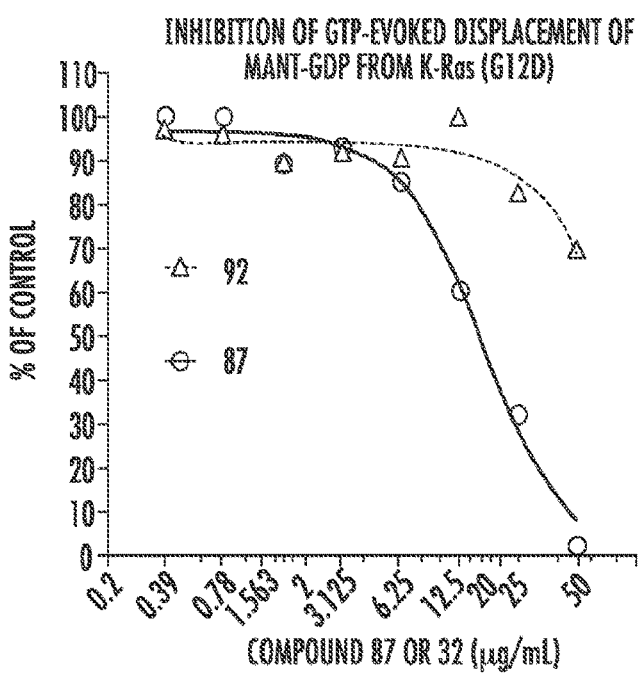
Figure 3C:
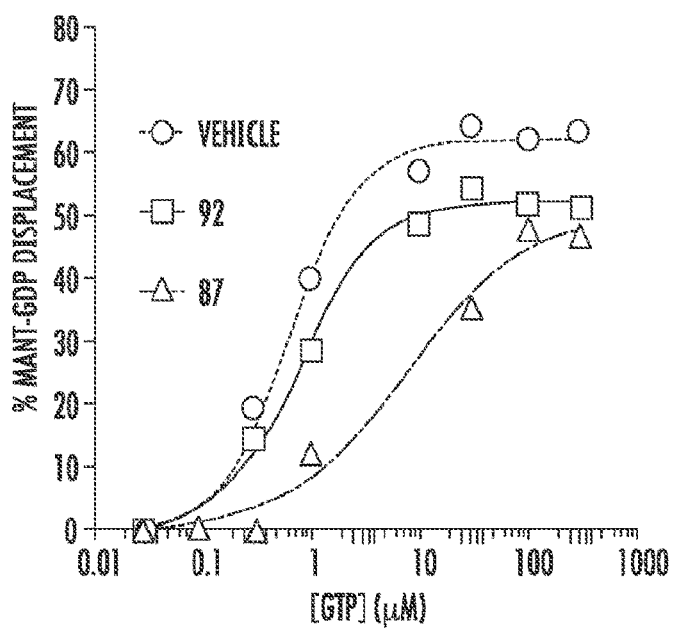

As shown in FIG. 2, the scaffold ranking library was used in the mant-GDP assay to identify chemical scaffolds that inhibit the ability of GTP to displace mant-GDP from mt G12D KRas. Focus was placed first on the most potent 2239 mixture sample, which contains 1,008 compounds that are all derived from the common imidazothiazole scaffold (FIG. 2). Screening of the positional scanning library for 2239, which consists of 66 mixtures that are systematically formatted with structural analogs as well as of selected individual compounds, led to several hits with the most potent, 87 (FIG. 3A), inhibiting the ability of GTP to displace mant-GDP from mt G12D KRas with $IC_{50}$ of 61 µM (FIG. 3B). A closely related analogue, 92, was much less active (FIG. 3B), suggesting that the methyl group or 92 was helpful to the binding. GTP titration curves show that in the absence of compounds, the $IC_{50}$ of GTP to displace mant-GDP was 0.62 µM, whereas in the presence of 87, the $IC_{50}$ was 13-fold higher at 7.2 µM (FIG. 3C). 92 had little effect on the ability of GTP to displace mant-GDP ($IC_{50}$=0.79 µM).

In addition, other hits were identified from the 2239 positional scanning library screens as well as from the original scaffold ranking library such as the sample mixture 2137 (dihydroimidazolyl-butyl-diketopiperazine scaffold) and sample mixture 2291 (disubstituted-Aryl-thiazole-piperazine scaffold) (FIG. 2).

When a cutoff value of 60% inhibition was used, the structures of these compounds are listed in FIG. 6.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating pancreatic, lung, or colon cancer in a subject, comprising administering to the subject in need thereof a compound having Formula I:

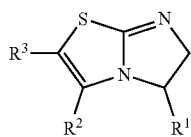

Formula I wherein
  $R^1$ is an alkyl group substituted with amino, alkoxyl, aryl, carbonyl, carboxylate, cyano, guanidinyl, halogen, haloalkyl, heteroaryl having 2-8 carbon atoms and 1-3 heteroatoms selected from O, N, or S, hydroxyl, nitrile, nitro, sulfinyl, sulfanyl, mercapto, ureylene, or ureido;
  $R^2$ is a phenyl group, optionally substituted with amino, alkyl, alkenyl, alkynyl, alkoxyl, aryl, carboxylate, cyano, guanidinyl, halogen, haloalkyl, heteroaryl having 2-8 carbon atoms and 1-3 heteroatoms selected from O, N, or S, hydroxyl, nitrile, nitro, sulfinyl, sulfanyl, mercapto, ureylene, or ureido;
  $R^3$ is H or an alkyl group;
or a pharmaceutical acceptable salt thereof.

2. The method of claim 1, wherein $R^3$ is alkyl.

3. The method of claim 1, wherein $R^2$ is unsubstituted phenyl.

4. The method of claim 1, wherein the compound has Formula IB

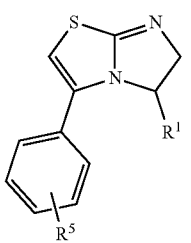

Formula IB wherein $R^5$ is hydrogen, amino, alkyl, alkenyl, alkynyl, alkoxyl, aryl, carboxylate, cyano, guanidinyl, halogen, haloalkyl, heteroaryl having 2-8 carbon atoms and 1-3 heteroatoms selected from O, N, or S, hydroxyl, nitrile, nitro, sulfinyl, sulfanyl, mercapto, ureylene, or ureido.

5. The method of claim 1, wherein $R^1$ is $C_{1-4}$ alkyl substituted with hydroxyl, guanidinyl, phenyl, hydroxyphenyl, tolyl, or heteroaryl.

6. A method for treating cancer in a subject, comprising administering to the subject a compound selected from any one of the following compounds

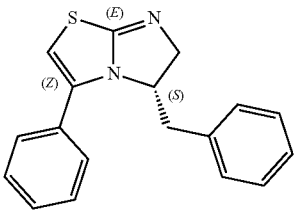

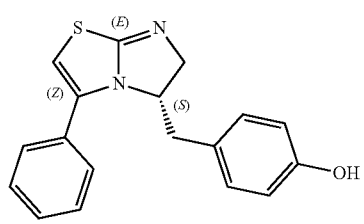

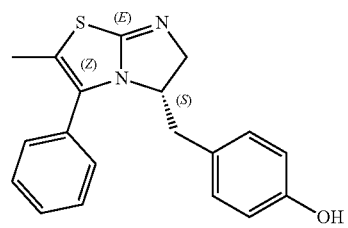

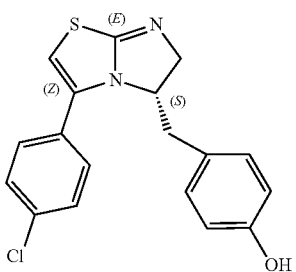

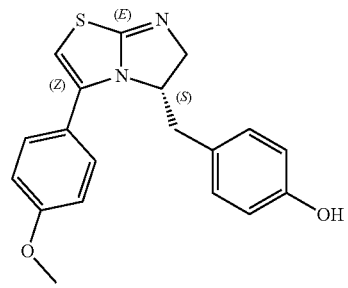

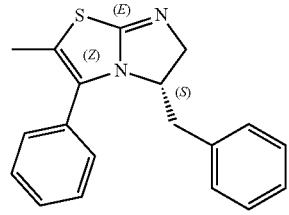

-continued
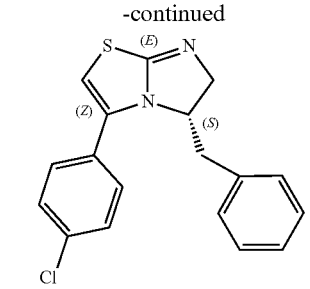
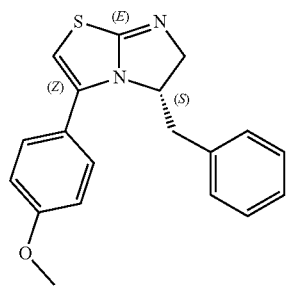
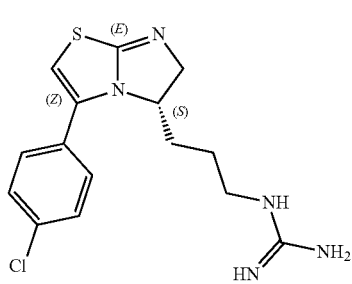
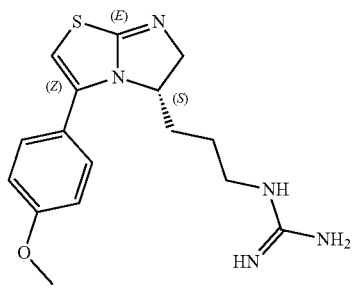
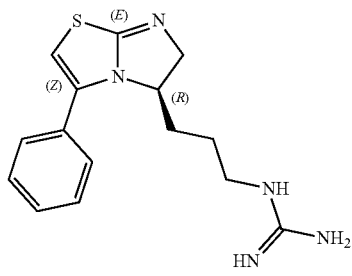
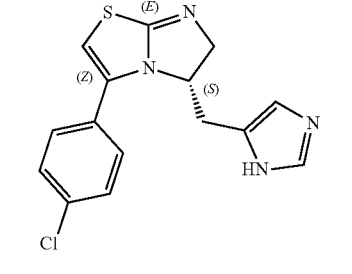
-continued
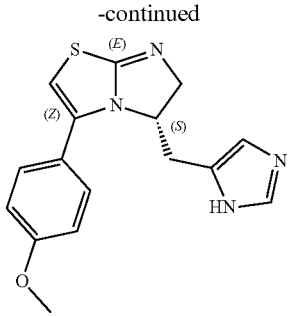
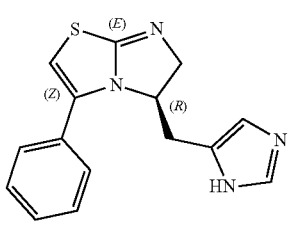
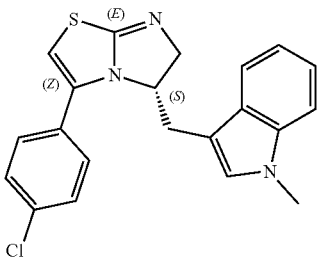
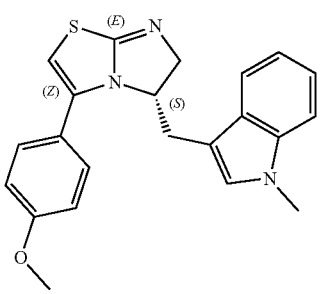
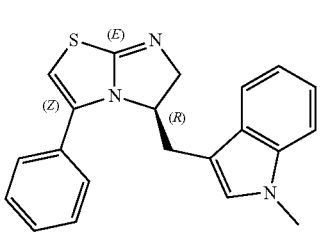
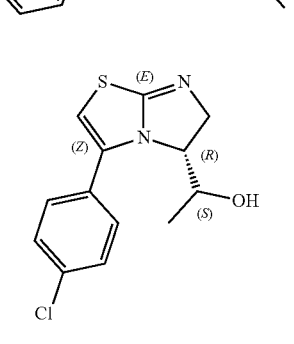

-continued
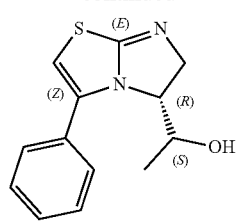
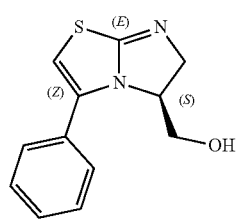
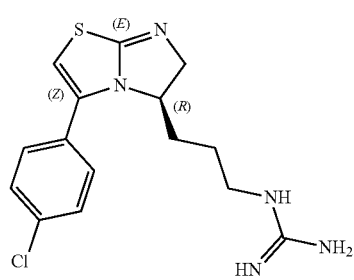
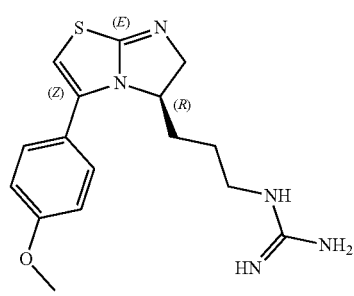
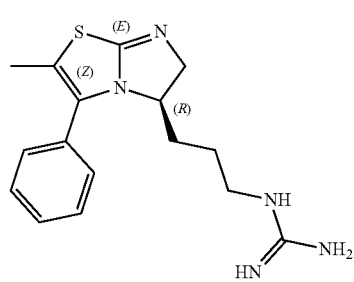
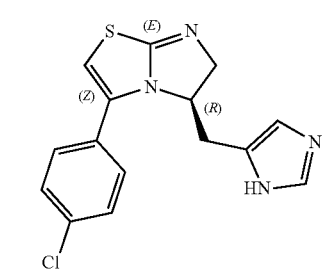
-continued
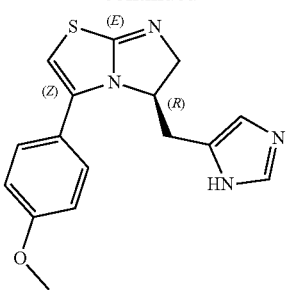
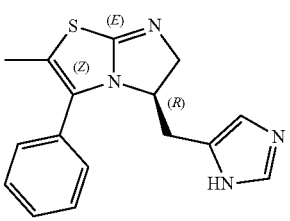
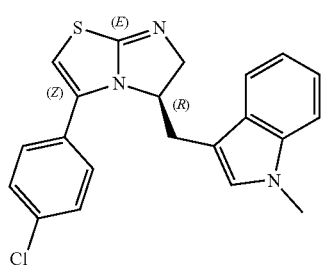
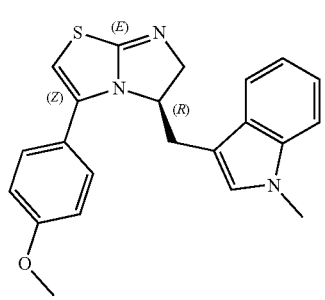
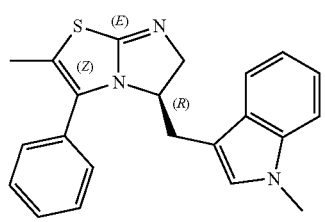
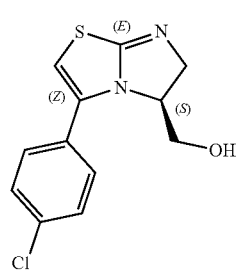

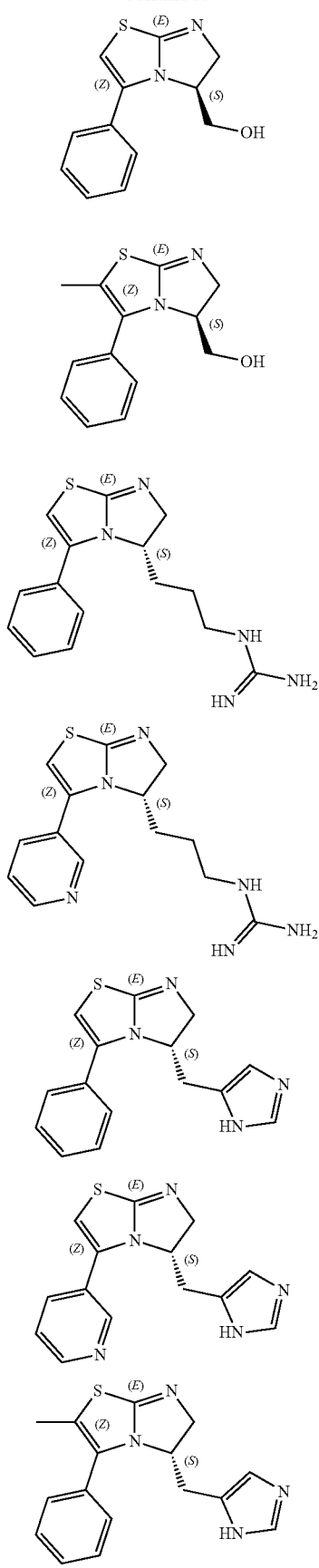
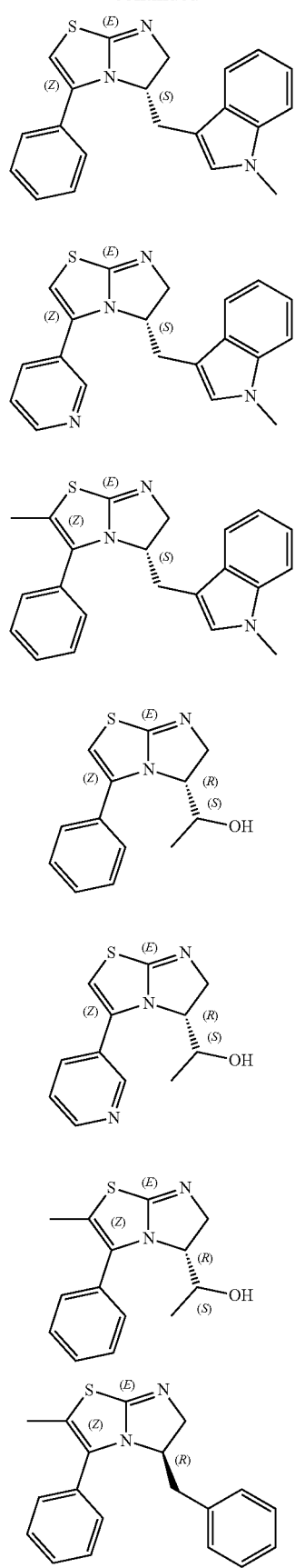

-continued

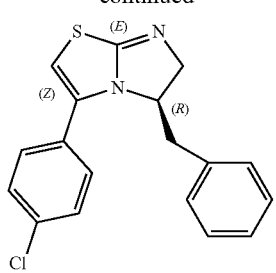
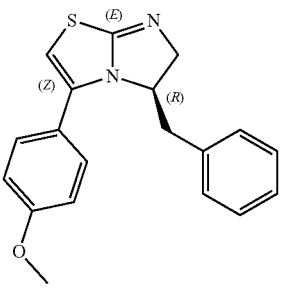
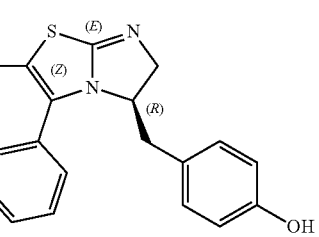
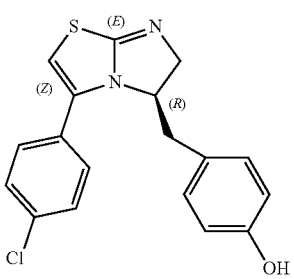
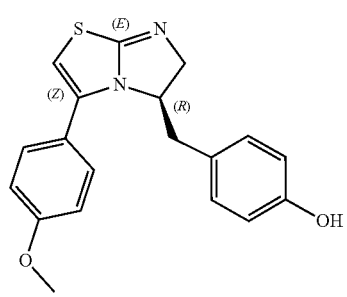
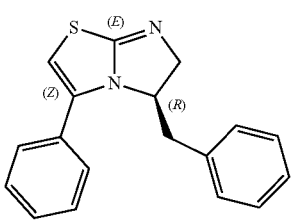

-continued

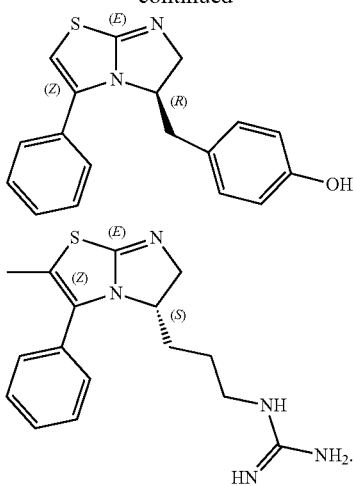

7. A compound having Formula I:

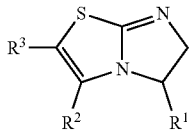

Formula I wherein
R$^1$ is an alkyl group substituted with amino, alkoxyl, aryl, carbonyl, carboxylate, cyano, guanidinyl, halogen, haloalkyl, heteroaryl having 2-8 carbon atoms and 1-3 heteroatoms selected from O, N, or S, hydroxyl, nitrile, nitro, sulfinyl, sulfanyl, mercapto, ureylene, or ureido;
R$^2$ is a phenyl group optionally substituted with amino, alkyl, alkenyl, alkynyl, alkoxyl, aryl, carboxylate, cyano, guanidinyl, halogen, haloalkyl, heteroaryl having 2-8 carbon atoms and 1-3 heteroatoms selected from O, N, or S, hydroxyl, nitrile, nitro, sulfinyl, sulfanyl, mercapto, ureylene, or ureido;
R$^3$ is H or an alkyl group;
or a pharmaceutical acceptable salt thereof, and optionally a pharmaceutically acceptable carrier.

8. The compound of claim 7, wherein R$^3$ is alkyl.

9. The compound of claim 7, wherein R$^2$ is unsubstituted phenyl.

10. The compound of claim 7, wherein the compound has Formula IB

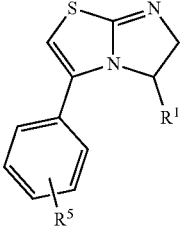

Formula IB wherein R$^5$ is hydrogen, amino, alkyl, alkenyl, alkynyl, alkoxyl, aryl, carboxylate, cyano, guanidinyl, halogen, haloalkyl, heteroaryl having 2-8 carbon atoms and 1-3 heteroatoms selected from O, N, or S, hydroxyl, nitrile, nitro, sulfinyl, sulfanyl, mercapto, ureylene, or ureido.
11. The compound of claim 7, wherein $R^1$ is $C_{1-4}$ alkyl substituted with hydroxyl, guanidinyl, phenyl, phenol hydroxyphenyl, tolyl, or heteroaryl.
12. A compound chosen from any one of the following compounds
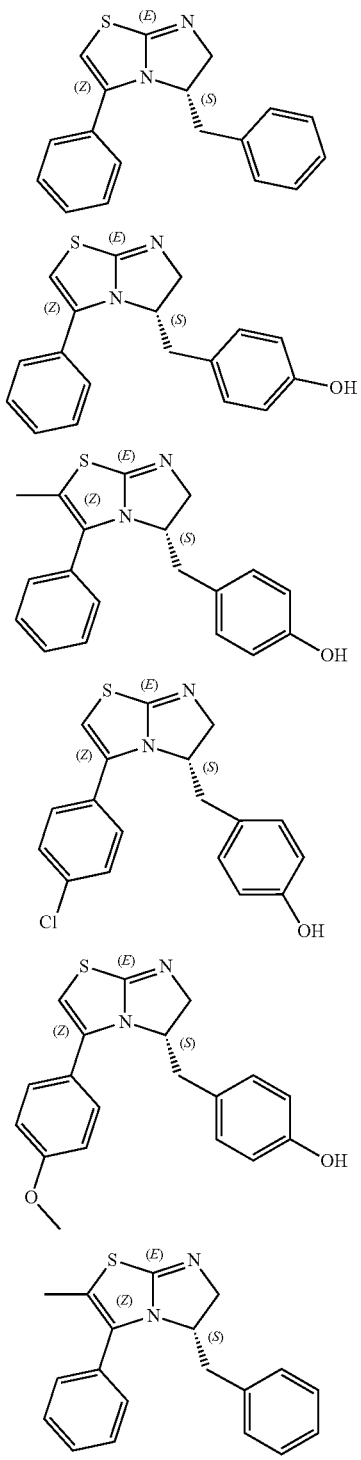
-continued
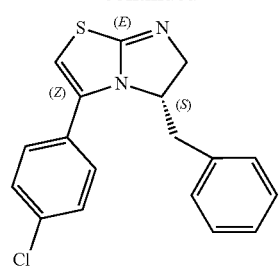
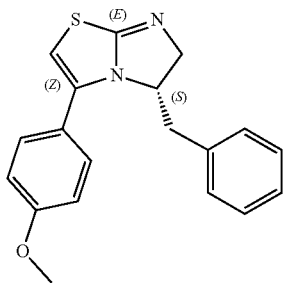
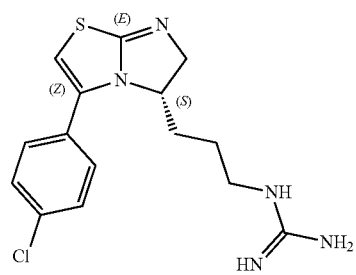
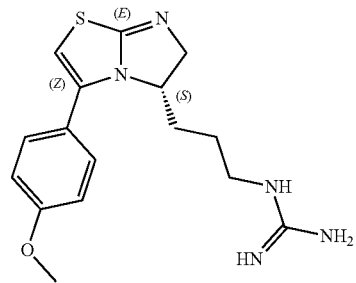
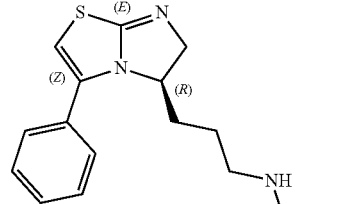
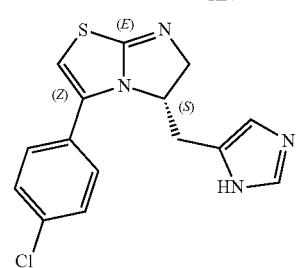

-continued
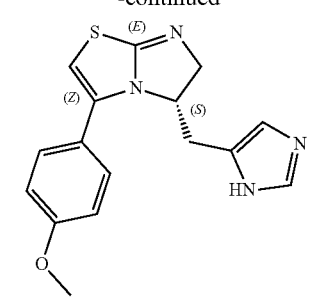
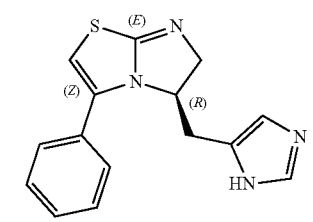
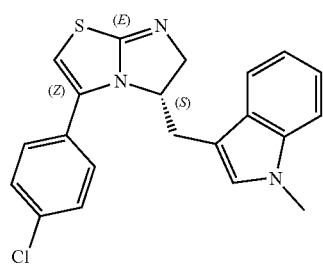
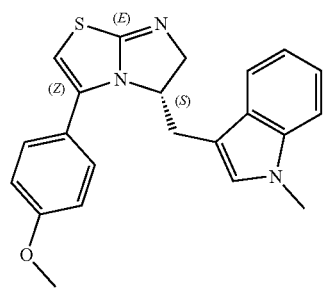
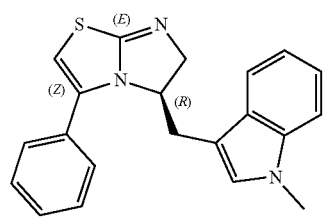
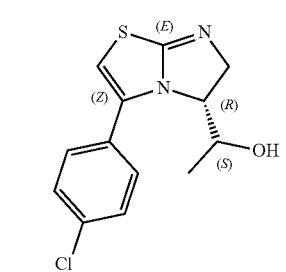
-continued
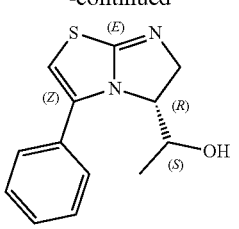
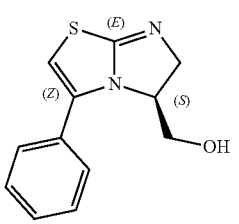
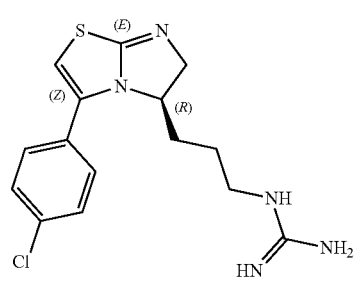
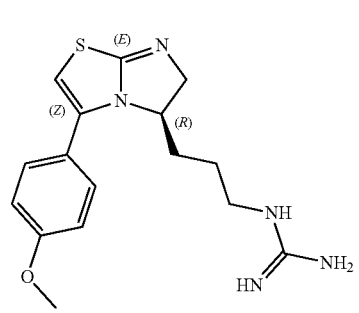
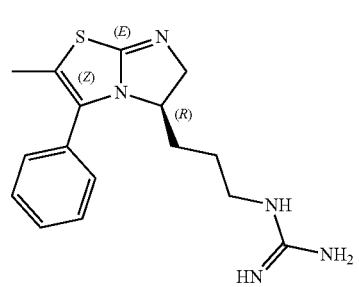
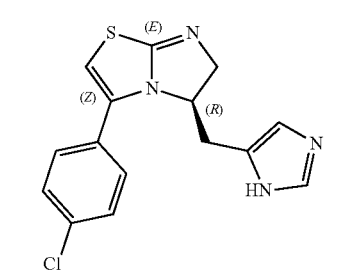

-continued
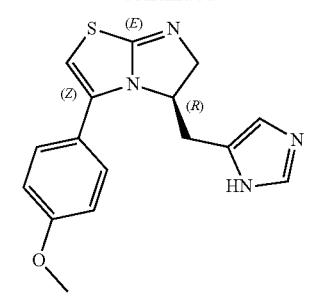
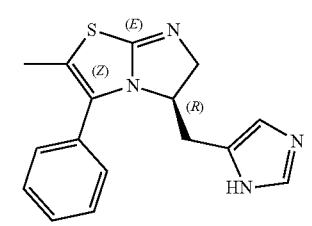
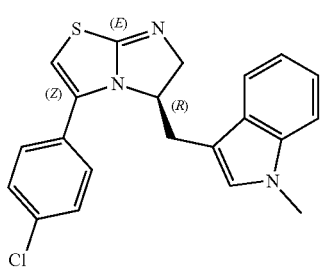
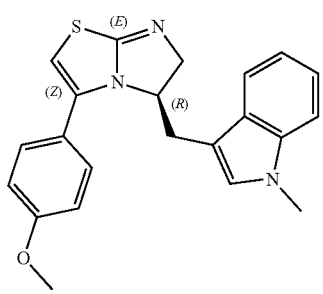
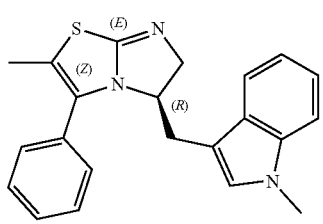
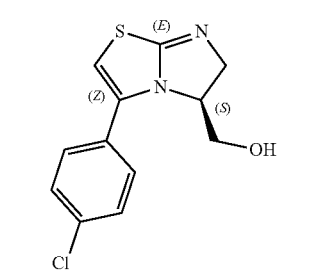
-continued
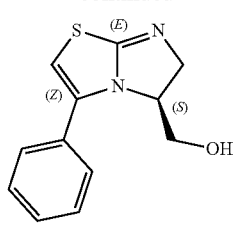
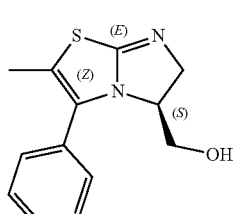
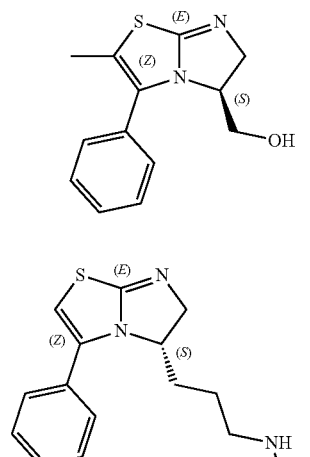
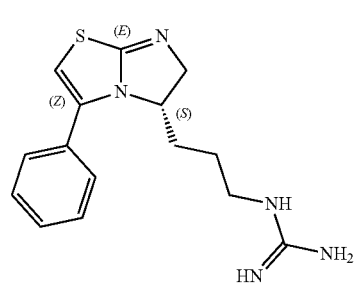
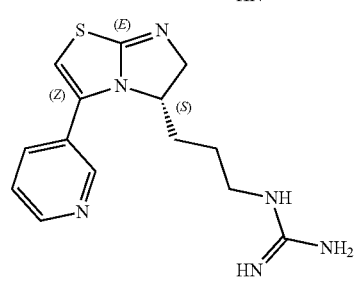
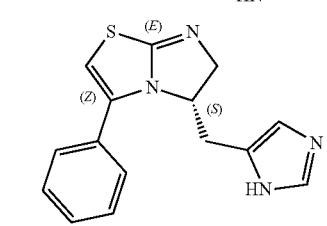
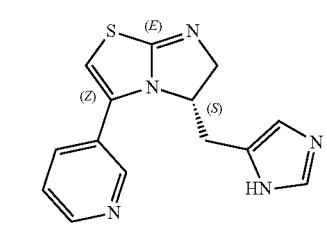
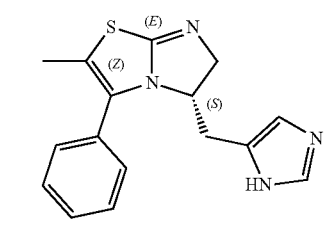

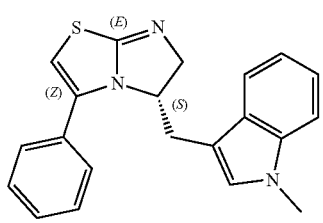
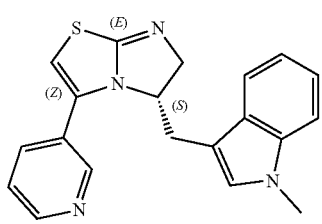
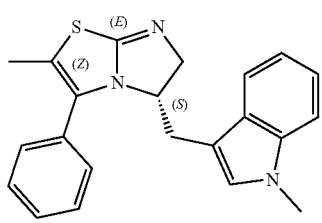
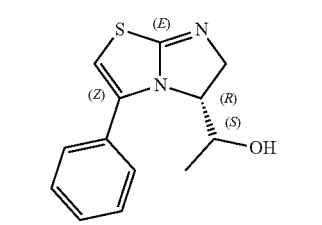
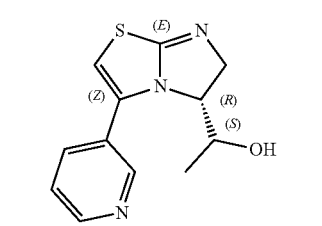
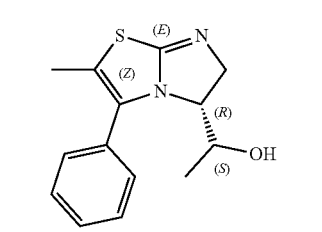
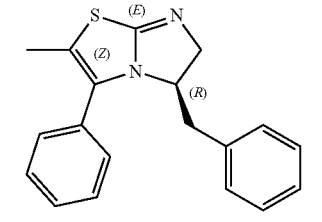
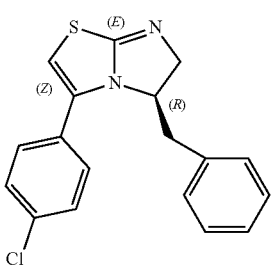
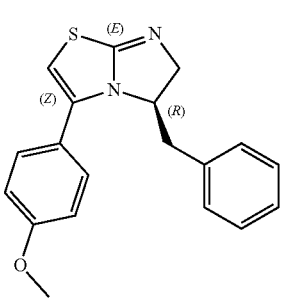
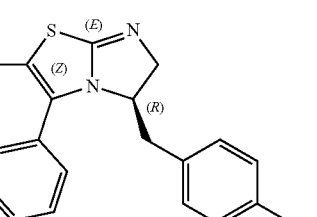
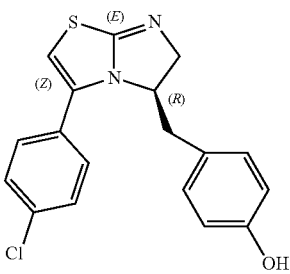
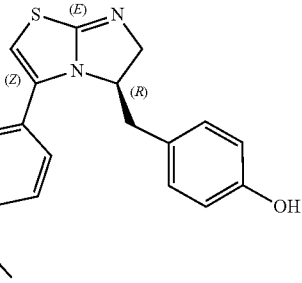
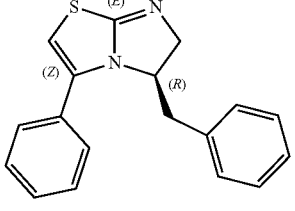

-continued

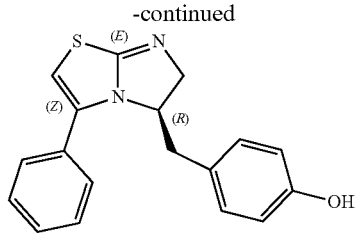

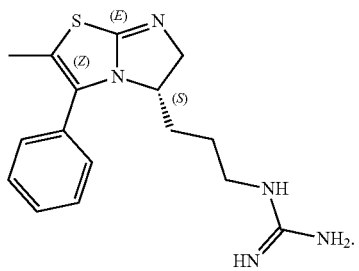

13. A pharmaceutical composition, comprising a therapeutically effective amount of a compound of claim 7 in a pharmaceutically acceptable excipient.

14. A pharmaceutical composition, comprising a therapeutically effective amount of a compound of claim 6 in a pharmaceutically acceptable excipient.

15. A pharmaceutical composition, comprising a therapeutically effective amount of a compound of claim 12 in a pharmaceutically acceptable excipient.

* * * * *

UNITED STATES PATENT AND TRADEMARK OFFICE
CERTIFICATE OF CORRECTION

PATENT NO. : 11,352,370 B2
APPLICATION NO. : 16/927517
DATED : June 7, 2022
INVENTOR(S) : Said M. Sebti et al.

It is certified that error appears in the above-identified patent and that said Letters Patent is hereby corrected as shown below:

In the Specification

In Column 1, Line 58, delete "assays" and insert --assays.--

In Column 6, Line 11, delete "acylamino," and insert --arylamino,--

In Column 8, Line 42, delete "1999" and insert --1999.--

In Column 9, Line 61, delete "C1-8" and insert --$C_{1-8}$--

In Column 9, Line 64, delete "R2" and insert --$R_2$--

In Column 9, Line 64, delete "substituted" and insert --substituted.--

In Column 11, Line 62, delete "Karposi's" and insert --Kaposi's--

In the Claims

In Column 29, Line 5 of Claim 11, delete "phenyl, phenol" and insert --phenyl,--

In Column 29, Line 8 of Claim 12, delete "compounds" and insert --compounds:--

Signed and Sealed this
Tenth Day of January, 2023

*Katherine Kelly Vidal*
*Director of the United States Patent and Trademark Office*